United States Patent [19]

D'Souza et al.

[11] Patent Number: 5,258,370
[45] Date of Patent: Nov. 2, 1993

[54] ARTIFICIAL REDOX ENZYMES

[75] Inventors: Valerian T. D'Souza; Ding Rong, both of St. Louis, Mo.

[73] Assignee: Curators of the University of Missouri, Columbia, Mo.

[21] Appl. No.: 680,511

[22] Filed: Apr. 4, 1991

[51] Int. Cl.$^5$ ............ A61K 31/715; A61K 37/48; C08B 30/18; C08B 37/16
[52] U.S. Cl. ......................... 514/58; 435/183; 435/188; 536/46; 536/103
[58] Field of Search ............ 514/58; 536/46, 103; 435/183, 188

[56] References Cited

U.S. PATENT DOCUMENTS

| | | | |
|---|---|---|---|
| 3,974,274 | 8/1976 | Kurita et al. | 514/58 |
| 4,592,996 | 6/1986 | Yamanishi et al. | 435/26 |
| 4,777,250 | 10/1988 | Bender et al. | 536/46 |
| 4,834,985 | 5/1989 | Elger et al. | 424/488 |
| 5,110,833 | 5/1992 | Mosbach | 530/387.1 |

OTHER PUBLICATIONS

J. Am. Chem. Soc., (1986), vol. 108, pp. 839–841 Cram et al.
Tabushi et al., J. Am. Chem. Soc. (1987) vol. 109, pp. 4734–4735.
Patent Abstracts of Japan, vol. 7, No. 213 (C-187) Sep. 20, 1983.
Hilvert et al., Bioorganic Chemistry, vol. 12, pp. 206–220 (1984).
Rong et al., Tetrahedron Letters, vol. 31, No. 30, Jul. 16, 1990, pp. 4275–4278.
Breslow, R., et al., J. Am. Chem. Soc., 100:3225-6 (1978).
D'Souza, V. T., et al., Biochem. Biophys. Res. Commun., 129:727–732 (1985).
Rao, K. R., et al., J. Chem. Soc. Chem. Commun., 0(1):10–11 (1990).
Breslow, R., et al., J. Am. Chem. Soc., 105:1390–1391 (1983).
Breslow, R., et al., Tetrahedron, 44:5515–5524 (1988).
D'Souza, V. T., et al., Acc. Chem. Res., 20:146–162 (1987).
Breslow, R., Cold Spring Harbor Symposium on Quantitative Biology, 52:75–81 (1987).
Breslow, R., Science, 218:532–537 (1982).
Royer, G. P., "Synthetic Enzyme Analogs (Synzymes)", Biotechnol., Ser. 5:297 (1985).
Breslow, R., Ann. N.Y. Acad. Sci., 471:60–69 (1986).
Breslow, R., "Artificial Enzymes and Enzyme Models", Adv. Enzymol. Relat. Areas Mol. Biol., 58:1–60 (1986).

Primary Examiner—Ronald W. Griffin
Attorney, Agent, or Firm—Rothwell, Figg, Ernst & Kurz

[57] ABSTRACT

Artificial redox enzymes are disclosed wherein one or more redox coenzymes or cofactors are linked to the 2-O, 3-O or 6-O positions of a D-glucopyranose ring of α-, β-, or γ-cyclodextrins. Also disclosed are facile synthetic methods for producing said artificial redox enzymes in good yield, and methods of use of such compositions.

26 Claims, 25 Drawing Sheets

α-cyclodextrin

ARTIFICIAL REDOX ENZYMES

BACKGROUND OF THE INVENTION

1. Field of the Invention

This invention relates to non-proteinaceous organic molecules that exhibit the catalytic and kinetic properties of enzymes. More particularly, this invention relates to cyclodextrin-coenzyme and cyclodextrin-cofactor conjugates that behave catalytically and kinetically as do oxidation-reduction ("redox") enzymes.

2. Description of the Related Art

Enzymes are proteins with catalytic activity that exhibit high specificity and large rate accelerations. Although enzymes are large and complex molecules, their power to catalyze chemical reactions can be attributed mainly to binding of reactants and catalysis. Binding not only is largely responsible for the specificity of the reaction but, by stereochemistry, also brings the substrate in close proximity to and in the correct orientation with the active site(s) of the enzyme. Other factors, such as the microenvironment of the catalytic site and the stabilization of the transition state by hydrogen bonding, contribute to enzyme activity, but binding (seen particularly in transition-state analogues) and catalysis are the two essential features of all enzymes. See, for a review of enzymes, Dixon, M., and Webb, E. C., *Enzymes*, Academic Press, N.Y., 1979.

An additional substance besides the enzyme and substrate is required in many cases in order that the reaction may proceed. Although such substances, variously referred to as 'cofactors' or 'coenzymes' may participate in the intermediate steps of the reaction catalyzed by the enzyme (or the cycle of reactions catalyzed by a system of enzymes), they are not consumed during the process, but are found in their original form at the end of the catalysis. They may, therefore, be regarded as an essential part of the catalytic mechanism.

The majority of coenzymes and cofactors act in one of the following ways: (a) as inter-enzyme carriers; (b) as a prosthetic group, which often is an intraenzyme carrier (e.g., heme, flavin, nicotinamide, pteridines, coenzyme Q, a metal atom or ion, etc.) covalently or electrostatically bound to the enzyme protein as an essential part of the enzyme; (c) by altering the shape of the enzyme molecule; (d) by subunit aggregation; (e) as stabilizers; (f) as templates; (g) as primers; and (h) as intermediates.

Enzymes are labile molecules, and this lability limits their industrial usefulness. They are sensitive to heat and pressures which, in the extreme, can reduce or destroy catalytic activity and, in the further extreme, can denature and precipitate the enzyme protein. Many enzymes are also sensitive to extremes of pH which can irreversibly inactivate the enzyme. The presence of proteolytic enzymes, whether of bacterial or other origins, will also reduce or destroy the effectiveness of enzymes. Certain heavy metal ions may also inactivate enzymes. For these reasons, non-protein artificial enzymes that are not subject to these problems have been sought for many years.

Non-protein artificial enzymes, also referred to as miniature organic models of enzymes, have been known since about 1970 when Breslow et al. disclosed an 'artificial enzyme combining a metal catalytic group and a hydrophobic cavity'. Breslow, R., et al., *J. Am. Chem. Soc.* 92:1075 (1970). See also, for a review: Breslow, R., *Cold Sorinq Harbor Symposium on Quantitative Biology*, 52:75–81 (1987).

As noted above, enzymes operate by binding a substrate and then performing a selective catalyzed reaction within the enzyme-substrate complex. The geometry of the complex and the geometric placement of various catalytic functional groups help determine both the rates and the specificities of the reaction. Among artificial enzymes, a generally useful type of binding appears to be hydrophobic inclusion within a cavity. Breslow et al., 1970 above, showed how hydrophobic binding in a cavity could be used to bring a simple organic compound close enough to a metal to permit metal-catalyzed reactions, even though the substrate itself is not a normal metal ligand.

The ideal artificial enzyme should not only have a cavity that provides maximum hydrophobic interaction with a substrate to form complexes, but the cavity should fit bulky components of the substrate such as aromatic rings, and orient the functional group of the bound substrate toward the attacking atom or group. D'Souza, V. T. et al., *Acc. Chem. Res.*, 20:146–152 (1987).

The cyclodextrins are cyclic molecules with a relatively hydrophobic interior cavity and hydroxyl groups that make them water soluble. Bender, M. L., et al., *Cyclodextrin Chemistry*, Springer-Verlag, N.Y. 1977; Tabushi, I., *Acc. Chem. Res.*, 15:66 (1982). Cyclodextrins consisting of 6 ($\alpha$-cyclodextrin or cyclohexaamylose), 7 ($\beta$-cyclodextrin or cycloheptoamylose) and 8 ($\gamma$-cyclodextrin or cyclooctaamylose) units of $\alpha$-1,4-linked D-glucopyranoses are known. Cyclodextrins have doughnut shapes with *secondary* hydroxyl groups at the C-2 and C-3 atoms of glucose units disposed in the more open end and *primary* hydroxyl groups at the C-6 atom of the glucose unit located at the other end (1).

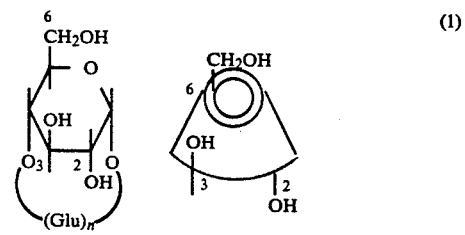

(1)

where n=6, 7 or 8. The interior of the cavity, consisting of a ring of C—H groups, a ring of glycosidic oxygen atoms, and another ring of C—H groups, is hydrophobic in nature. The inner diameters of the cavities are approximately 4.5 Å in $\alpha$-cyclodextrin, 7.0 Å in $\beta$-cyclodextrin and 8.5 Å in $\gamma$-cyclodextrin. D'Souza et al., 1987, above. $\alpha$- and $\beta$-Cyclodextrins would provide a snug fit for an aromatic ring. Formation of inclusion complexes with various substrates (binding) is one of the most important characteristics of cyclodextrins. Bender, M. L., et al., *Adv. Enzymol. Relat. Areas Mol. Biol.*, 58:1 (1986).

Breslow et al. (Breslow, R., et al., *J. Am. Chem. Soc.*, 105:1390–1391 (1983)), have produced a 'synthetic transaminase' enzyme wherein the coenzyme pyridoxamine is linked to the C-6 of $\beta$-cyclodextrin, thereby putting it on the more narrow *primary* end of the structure. The artificial enzyme is reportedly able to transaminate keto acids, with a preference for keto acids containing an hydrophobic aromatic group, e.g., phenylpyrunic acid. The coenzyme was also attached to the *secondary* face of the molecule via the C-3 hydroxyl group, but, although this molecule reportedly also catalyzes transamination and also prefers aromatic keto acids as substrates, the secondary-side derivative is only about half as effective as is the primary side analogue. Further, the primary-side derivative gives a preference for the synthesis of the natural (in vertebrates) L-enantiomers of amino acids, whereas the secondary-side derivatives give a preference for the synthesis of the unnatural D-product.

D'Souza et al. (D'Souza, V. T., et al., *Biochem. Biophys. Res. Commun.*, 129:725 (1985)) have synthesized a 'synthetic chymotrypsin' proteolytic enzyme wherein α, β and γ-cyclodextrins are functionalized by derivatization at the *secondary-side* 2-hydroxyl group with o-[4(5)-mercaptomethyl-4(5)-methylimidazol-2-yl] benzoic acid, to produce a derivative designed to mimic the active site of chymotrypsin itself. The artificial and natural enzymes are reportedly comparable in their catalytic activity. Further, whereas the real chymotrypsin has an optimal temperature around 45° C., it precipitates after about 55° C. and is rendered inactive; in contrast, the activity of the artificial enzyme keeps increasing to at least 80° C.

Breslow et al. (Breslow, R., et al., *J. Am. Chem. Soc.*, 100:3225 (1978)) constructed β-cyclodextrinyl bisimidazole which is a model for the ribonuclease enzyme. In this artificial enzyme, the bisimidazole is linked to two of the *primary-side* 6-hydroxyl groups of the β-cyclodextrin, forming a bifunctional catalytic site. The artificial enzyme was reportedly slow compared to ribonuclease itself, although exhibiting characteristics of the enzyme.

The class of protein enzymes referred to variously as oxidoreductases or redox enzymes includes enzymes concerned with biological oxidation and reduction, and therefore with respiration, fermentation, and metabolism in general. Oxidoreductases include (a) dehydrogenases and oxidases that employ, e.g., AND, NADP, FMN and electron-transferring flavoproteins, as coenzymes; (b) peroxidases that can be iron-containing heme proteins or flavoproteins; and (c) oxygenases or hydroxylases that can be flavoproteins, use pteridines or 2-oxoglutamate as coenzymes, or use copper ions as an oxidation / reduction pair. Such enzymes have great medical and industrial potential. However, such applications are limited by the instability of these enzymes to high temperatures and pressures, mechanical stress, organic solvents and detergent conditions. Thus, artificial redox enzymes that carry out the catalytic functions of natural redox enzymes but that are stable to the conditions noted above, would be extremely valuable.

Limited success has been achieved with an artificial flavoenzyme. Tabushi et al. (Tabushi, I., et al., *J. Am. Chem. Soc.*, 109:4734–4735 (1987)) reported the synthesis of an artificial flavoenzyme, flavo-α-cyclodextrin in which the 8-position of the flavin is attached to the *primary-side* 6-position. This molecule reportedly carries out electron transport, although it was also disclosed in this report that the natural NADH-dependent flavoprotein enzyme exhibits a rate constant 30-fold greater than that of the artificial enzyme, and the natural flavoprotein exhibits an association constant for NADH 8-fold greater than does the artificial enzyme. In addition, the reported chemical synthesis of this artificial is difficult, as the riboflavin decomposes under the mildly basic conditions that are required to attach the coenzyme to the 6-position of cyclodextrin by the disclosed process (see below in Detailed Description of the Invention).

Thus, a great need exists for highly active and stable, readily and inexpensively synthesizable artificial redox enzymes. This need has been fulfilled by the invention disclosed below.

SUMMARY OF THE INVENTION

We have chemically synthesized artificial redox enzymes comprising derivatives of cyclodextrins that catalyze the same reactions as do natural protein redox enzymes, such as oxidation and hydride transfers, but which are devoid of the limitations of protein enzymes such as instability in the presence of high temperatures or pressures, mechanical stress, organic solvent and detergent conditions, and proteolytic enzymes.

It is thus an object of this invention to provide novel artificial redox enzymes.

It is another object of this invention to disclose the chemical synthesis of such novel artificial enzymes.

It is yet another object of this invention to disclose uses to which these artificial enzymes may be put.

It is still another object of this invention to disclose means for altering the solubility characteristics of cyclodextrin artificial redox enzymes.

These and other objects will become apparent by reference to the specification and to the appended claims.

DETAILED DESCRIPTION OF THE INVENTION

We have invented useful and novel artificial redox enzymes and methods for the chemical synthesis of such molecules based on the chemistry of biological redox enzymes.

As noted above, binding and catalysis are the major features that enable protein enzymes to bring about chemical transformations with large acceleration and high specificity. D'Souza et al. 1987 above. Binding anchors the substrate molecule at the site at which the reaction is intended to occur and catalysis lowers the energy barrier of the reaction and enables the reaction to occur at lower temperatures and at a faster rate. The artificial redox enzymes designed and synthesized here contain a binding site to bind specific substrates and a catalytic site to catalyze redox reactions.

Figure 1:
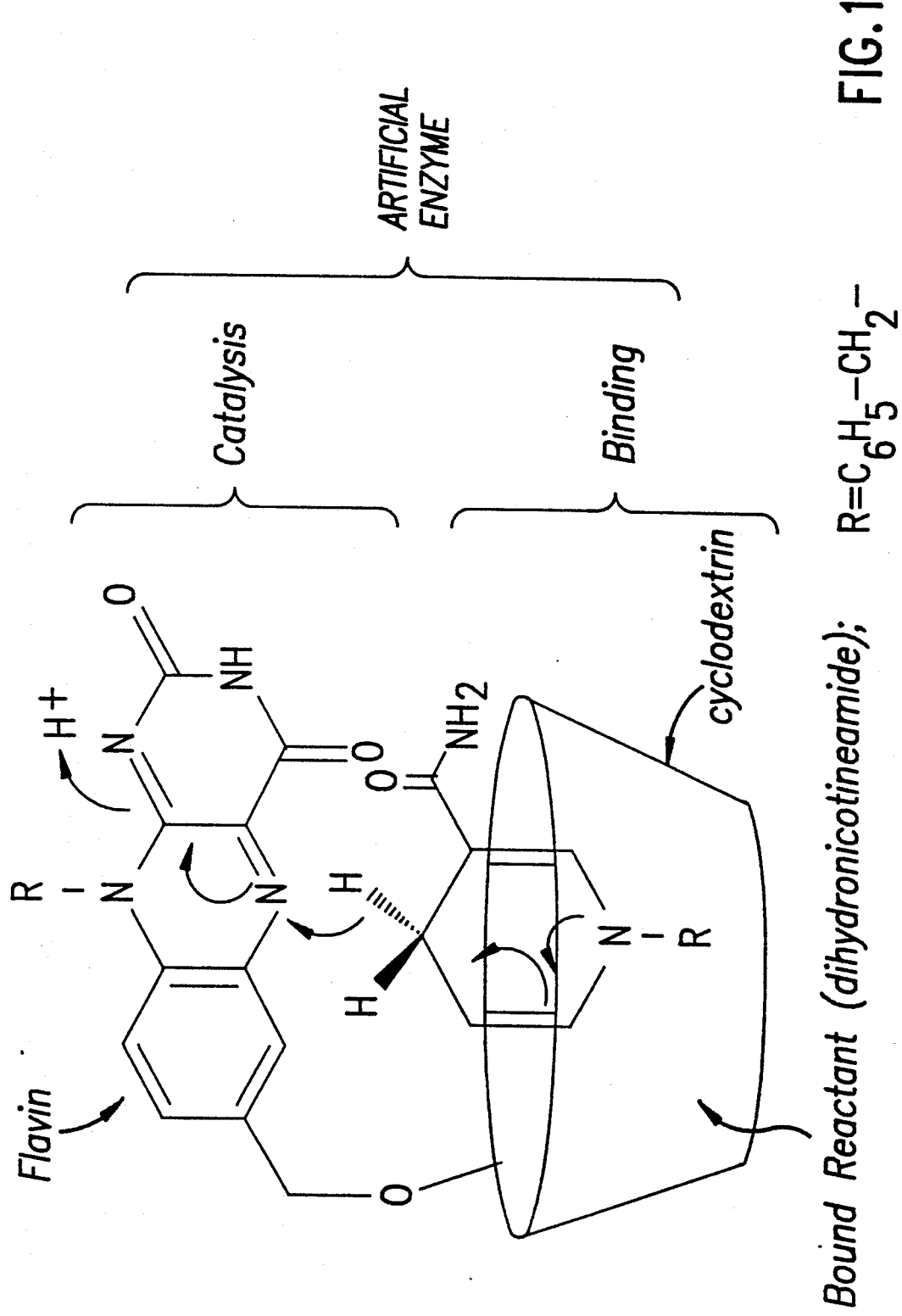
FIG. 1 shows the structure of a flavocyclodextrin artificial enzyme bound to a dihydronicotinamide substrate.

A schematic drawing of one such novel artificial redox enzyme is shown in FIG. 1. In this molecule, dihydropyridine (the 'working end' of AND and NADP) non-covalently bound to cyclodextrin is shown as being oxidized by hydride ion transfer to a flavin covalently attached to the *secondary* side of cyclodextrin.

As the secondary side of cyclodextrin is the preferred side for the binding of substrates (Van Etten, R. C., et al., *J. Am. Chem. Soc.*, 69:3242 (1967)), it is an important aspect of this invention that the novel flavocyclodextrins, wherein the flavin moiety is attached to this side, act as a more efficient artificial redox enzyme than do their *primary* side counterparts.

Flavin is a co-factor in seven categories of enzymes: dehydrogenases, oxidases, oxido-decarboxylases, monooxygenases, dioxygenases, metalloflavoenzymes and flavodoxins. These enzymes catalyze a variety of chemical transformations such as those shown in Table 1. Thus, the artificial flavoenzymes described here will be invaluable in processes such as those that require the chemical transformations listed in Table 1.

The synthesis of 6-flavo-α-cyclodextrin according to Tabushi et al. 1987, above, did not yield product. 6-Deoxy-6-thioaceto-β-cyclodextrin (1), synthesized from the known 6-tosyl-β-cyclodextrin (Melton, L. D., et al., *Carb. Res.*, 19:29 (1971) and potassium thioacetate, was hydrolyzed to 6-deoxy-thio-β-cyclodextrin (2). The physical constants and $^1$H NMR spectra of 2 were identical to those previously reported (Fujita, K., *Biorg. Chem.*, 11:73 (1982); D'Souza, V. T., et al., 1985 above). 2 was allowed to react with 8-α-bromo-2',3',4',5'- tetracetylriboflavin (Br T fl) (Lemuel, B. W. et al., *J. Mol. Cat.*, 9:209 (1980); Walker, W. H., et al., *Eur. J. Biochem.*, 26:279 (1972)) under a variety of conditions.

TABLE 1

Biochemical transformations involving flavin coenzyme

| Chemical transformation | Examples |
|---|---|
| −C−OH → C=O | D-Lactate dehydrogenase, Glucose oxidase, Thiamine dehydrogenase |
| −CH−NH$_2$ → C=O + NH$_4^+$ | D- and L-amino-acid oxidases, Amine oxidases |
| −CH−CH−C=O → C=C−C=O | Succinate dehydrogenase, Acyl-CoA dehydrogenase, Dihydroorotate dehydrogenase |
| NADH → NAD$^+$ | NADH dehydrogenase, transhydrogenases, Dihydroorotate dehydrogenases, NADH-dependent monooxygenases |
| HS SH → S—S | Lipoamide dehydrogenase, Glutathione reductase |
| R-Ph-OH → R-Ph(OH)-OH | p-Hydroxybenzoate hydroxylase, Phenol hydroxylase |
| cyclopentanone → δ-valerolactone | Cyclopenatanone monooxygenase |
| R−CHO → R−COO$^-$ | Luciferase |

Although TLC data indicated that some reaction has taken place, $^1$H and $^{13}$C NMR spectra of the isolated products indicated a mixture of compounds formed by decomposition of flavin and unreacted 2.

An attempt was made to synthesize 6-flavo-β-cyclodextrin by a nucleophilic attack of a flavin derivative on 6-iodo-β-cyclohdextrin 3 in Scheme I below. However, the synthesis of the nucleophilic flavin derivative, 8-α-thio-tetracetylriboflavin, by the reaction of potassium thioacetate with BrTfl and subsequent hydrolysis failed. The flavin derivative decomposed during the initial reaction, and no product could be detected. We discovered that flavin derivatives decomposed rapidly even under mildly basic conditions, and this property makes unusable previously reported methods of synthesizing flavocyclodextrins (Tabushi et al., 1987, above).

In the following disclosures, cyclodextrin will be abbreviated as CD.

We have discovered a superior and facile method for the synthesis of flavocyclodextrins which involves constructing the flavin moiety from precursors previously attached to the CD. In Scheme I, below, reaction of 6-iodo-CD (3) with o-phenylenediamine will yield 6-(o-phenylenediamino)-CD (4). Reaction of 4 with alloxan monohydrate will produce the desired flavo-CD (5). The α-1,4-glycosidic bonds of CD will not hydrolyze under acidic reaction conditions. The 6-flavo-β-CD thus obtained can be analyzed by ¹H and ¹³C NMR.

N-alkyl-5-haloalkyl-2-nitroaniline, N-aryl-5-haloalkyl-2-nitroaniline, N-alkyl-2-amino-5-haloalkylaniline, N-aryl-2-amino-5-haloalkylaniline, N-alkyl-6-haloalkyl-2-nitroaniline, N-aryl-6-haloalkyl-2-nitroaniline, N-alkyl-2-amino-6-haloalkylaniline, N-aryl-2-amino-6-haloalkylaniline, haloalkyl, (haloalkyl)aryl, alkylsulfonyl halide, arylsulfonyl halide, acyl halide, acyl anhydride, acid halide, acid anhydride, and alkylepoxide. Suitable substituents on the phenyl moiety in accordance with this invention may include alkyl, aryl, halo, amino, and mono- and di-substituted amino groups.

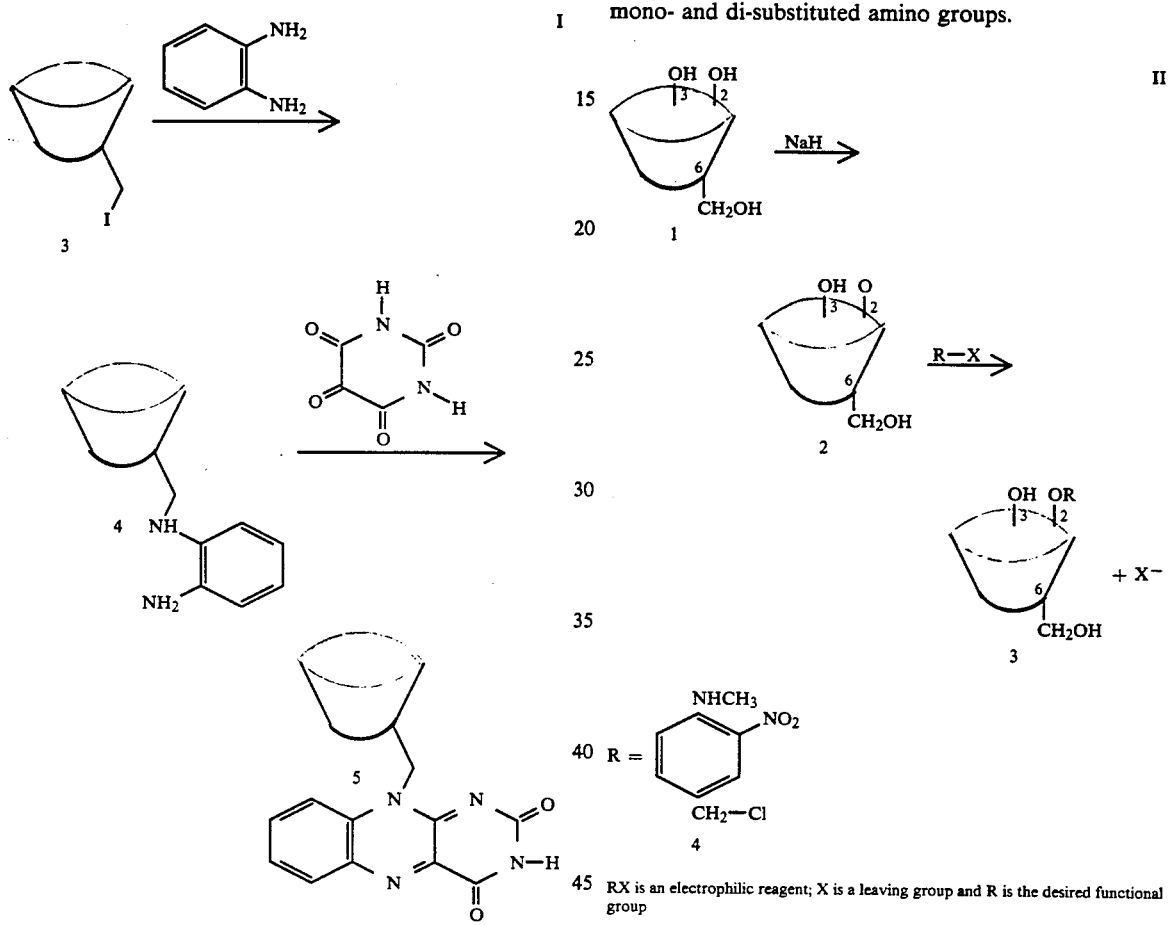

RX is an electrophilic reagent; X is a leaving group and R is the desired functional group The more-important and preferred 2-flavo-CD's can be synthesized as shown in the general method of Scheme II. It involves the removal of a single proton from the hydroxyl group at the 2-position of CD (1) based on its acidity using dry DMF and NaH to yield (2), followed by a nucleophilic substitution of the resultant oxyanion by the desired electrophile to give CD mono-substituted at the 2-O position (3). This method is a general method that can be used to attach any catalytic site to the more important catalytically *secondary* side of CD's. Other suitable hydroxyl proton removing reagents include metal hydroxides, metal alkoxides, alkali metals, and organometallic compounds. Suitable RX electrophilic reagents include phenyl unsubstituted or substituted N-alkyl-4-haloalkyl-2-nitroaniline, N-aryl-4-haloalkyl-2-nitroaniline, N-alkyl-2-amino-4-haloalkylaniline, N-aryl-2-amino-4-haloalkylaniline, N-alkyl-2-amino-4-haloalkylaniline, N-aryl-2-amino-4-haloalkylaniline, N-alkyl-3-haloalkyl-2-nitroaniline, N-aryl-3-haloalkyl-2-nitroaniline, N-alkyl-2-amino-3-haloalkylaniline, N-aryl-2-amino-3-haloalkylaniline, An example of the construction of the flavin moiety on the secondary side of CD is shown in Scheme III.

4-Chloro-3-nitro-benzaldehyde is reacted with methylamine to yield 4-(methylamino)-3-nitrobenzaldehyde (8) which is then reduced by NaBH₄ to N-methyl-4-hydroxymethyl-2-nitroaniline (9). Reaction of SOCl₂ with 8 will give N-methyl-4-chloromethyl-2-nitroaniline (10). Structures of 8, 9 and 10 may be characterized by ¹H NMR and elemental analysis. 10 is used as an electrophile to react with sodium CD alkoxide (11) to yield 2-O-(4-methylamino-3-nitro) benzyl-β-CD (12). The addition of 10 to 11 is a novel method for monofunctionalizing the 2-position of CD's (Rong, P., and D'Souza, V. T., *Tetrahedron Lett.*, 31:4275 (1990)). 12 is hydrogenated by agents such as H₂/Pd, H₂/Pt, H₂/Ni, Sn/HCl, Fe/HCl and Zn/HCl, and then condensed with alloxan monohydrate to yield 2-flavo-CD (13). Compounds 11 and 12 can be characterized by ¹H and ¹³C NRM. 2-Flavo-α-CD, β-CD and γ-CD may be synthesized by the same method.

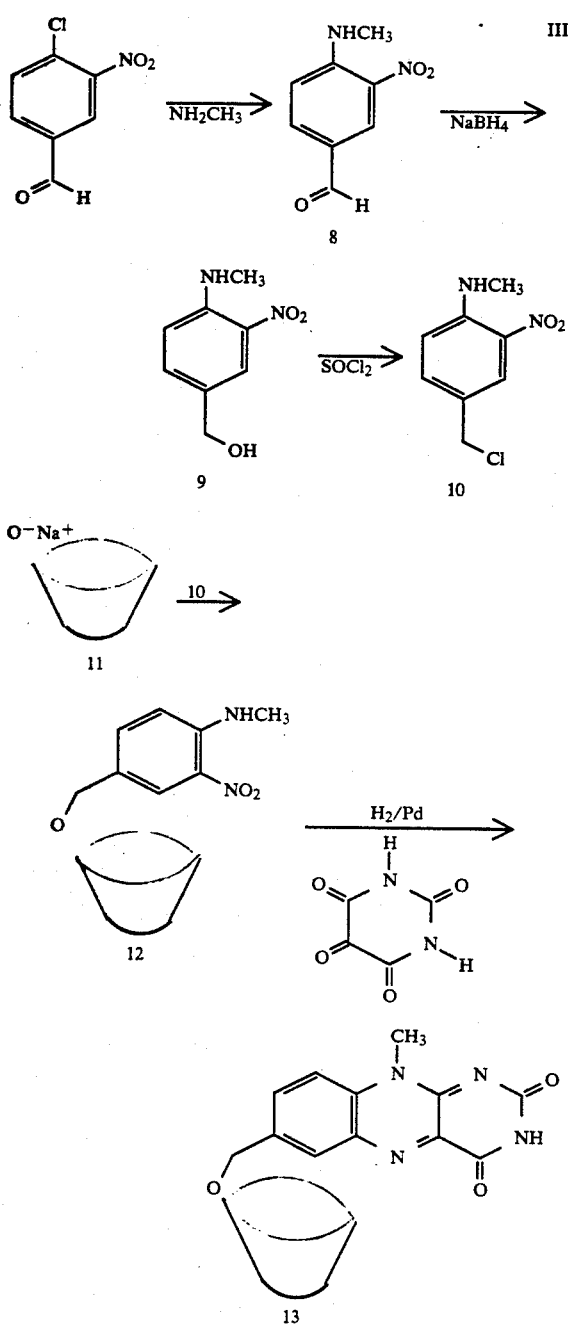

The most important feature of this synthesis is the condensation of alloxan with the substituted diamine under acidic conditions. Contrary to theoretical expectations, CD was found to be stable under such conditions, and produces good yields of isolated and purified flavin 13. This has opened a new and simple route for the synthesis of modified flavo-CDs by condensing a modified alloxan with 2-O-(4-methylamino-5-nitro) benzyl-CD, 12. Although the general reaction is exemplified with 2-O-(4-methylamino-5-nitro) benzyl-CD (12), any benzyl derivative may be used provided that there is a nitro group ortho to the amino group.

Many modifications of this basic invention are possible without departing from the concept and scope of this invention. For example, the flavin molecule may be attached to the *secondary* side of a CD, and all of the remaining hydroxy groups may be derivatized to, e.g., O-alkyl, O-acyl, O-aryl, O-alkylsulfonyl, O-arylsulfonyl or O-(trialkylsilyl) groups. This will increase the hydrophobicity of the artificial enzyme, thereby increasing the reactivity with hydrophobic substrates and increasing the solubility of the artificial enzyme in less-hydrophilic solvents. In addition, an N-alkyl substituted alloxan, e.g., N-methylalloxan, can be used instead of alloxan to increase the stability of the artificial redox enzyme. Other suitable $N_3$-substituent groups on the alloxan include aryl, acyl, alkylsulfonyl and arylsulfonyl groups. The chain length of the linker between the CD and the flavin may be varied by using higher homologues of the benzyl chloride derivative 10. Alkyl groups other than methyl, as well as aryl, chloro, bromo, iodo, fluoro, amino, and mono- and di-substituted amino groups, may be used as substituents on the amino group of the o-phenylenediamine moiety.

Although flavo-CD artificial redox enzymes have been used to illustrate this invention, it should be emphasized that the concept of the invention is generally applicable to any artificial redox enzyme using CD as the matrix. For example, covalently bound coenzymes such as nicotinamide, heme, pteridines, and coenzyme Q and electrostatically bound cofactors such as chromium, manganese, iron, cobalt, nickel, copper, zinc, rhodium, osmium, palladium and platinum ions may be bound to the *primary* or *secondary* sides of a CD molecule in order to carry out appropriate redox reactions.

Although it has been convenient to illustrate the artificial redox enzymes of the invention with a single coenzyme covalently bound to one or another ring carbon atom of the glucopyranose of a cyclodextrin, it is within the spirit and scope of the invention to have two or three different redox coenzymes and cofactors linked to the same or other glucopyranose rings at different positions, i.e., at the 2-, 3-, and 6-positions. Such multiple coenzymes may be used to carry out sequential reactions in a synthetic scheme, such as an oxidation at the site and substrate subsite of one coenzyme and a reduction of the product at a different pair of sites using a second coenzyme or cofactor. For example, pairs or triplets of the aforementioned redox coenzymes and cofactor metal ions may be attached to appropriate positions on one or more glucopyranose rings of cyclodextrins to carry out sequential redox reactions.

The artificial redox enzymes of the invention have particular utility as industrial catalysts. That is, they may advantageously be employed to carry out oxidations and/or reductions in synthetic processes, and, because of their inherent stability relative to their natural counterpart enzymes, they may be employed in high temperature or pressure applications, thereby increasing yields of products. For example, the artificial enzymes of the invention may be attached to the inner surface of a thermojacketed tube, the reactants pumped through the tube at appropriate rates and with appropriate means to place reactants in contact with the artificial enzymes, and products drawn off at the other end of the tube. Alternately, the artificial enzymes of the invention may be used in a batch mode, wherein the artificial enzyme(s) is (are) attached to the inner surface of a thermojacketed reaction vessel, reactants added with mixing, and products isolated from the reaction mixture.

Such artificial catalysts of the invention may also be used to perform reactions for which no natural enzymes occur. Many of the most important chemical processes of interest in chemical manufacturing, for instance, are not processes that are performed enzymatically in nature. However, appropriate artificial redox enzymes could be prepared by the methods of the invention, and these compositions could in principle perform these useful chemical reactions with an enzymatic style and with the resultant advantages of selectivity and rate characteristic of this style.

The examples that follow provide several embodiments of the synthetic routes to the artificial redox enzymes of the invention, the chemical and physical properties of such compositions, and the kinetic properties of the molecules. These examples are illustrative only and are not intended in any way to limit the scope of the invention, which is provided by the specification and appended claims.

EXAMPLE I

Synthesis of Mono-6-flavo-β-cyclodextrin 5

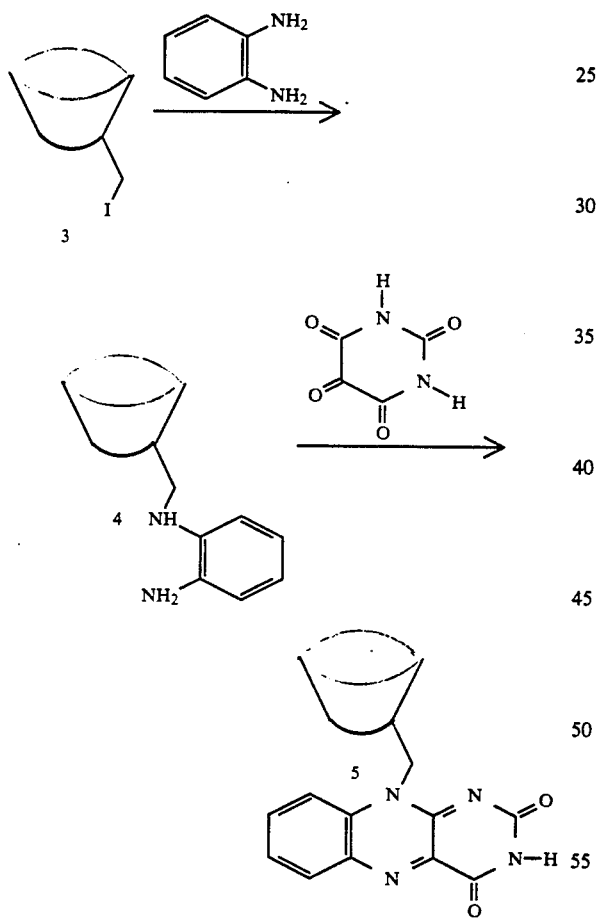

$^1$H and $^{13}$C NMR spectra were obtained from a Varian XL-300 spectrometer. TMS was used as an internal reference when the CDCl$_3$ or DMSO-d$_6$ was the solvent. TMS was used as an external reference when D$_2$O was the solvent. All the R$_f$ values were obtained using TLC on silica plates with the solvent: n-butanol:ethanol:water=5:4:3 by volume.

6-Mono-tosyl-β-cyclodextrin. It was synthesized according to Saenger, W., *Angew. Chem. Int. Ed.*, 19:334 (1980).

Mono-6-O-iodo-β-cyclodextrin (3). It was synthesized by the reaction of 5.0 g (30 mmol) of potassium iodide with 1.9 g (1.5 mmol) of 6-tosyl-β-cyclodextrin in 100 ml DMF at 80° C. for 2.5 hours. After the volume of the solution was reduced to 6 ml by evaporation, 200 ml of absolute ethanol was added and then stirred overnight. Collection of the precipitate formed gave 3 in a pure form.

Mono-6-0-(o-phenylenediamino)-β-cyclodextrin (4). 3, 2.2 g (1.8 mmol), was reacted with 4.4 g (41 mmol) of o-phenylenediamine in DMF at 110° C. for 3 hours under nitrogen. The product formed was precipitated with 400 ml acetone. After filtration, the precipitate was redissolved in 40 ml water and then extracted with 50 ml chloroform. After addition of 300 ml acetone to the aqueous layer, the precipitate was collected to yield 2.1 g (94%) of 4. TLC of the product indicated a single compound. $^1$H and $^{13}$C NMR spectra indicated that one o-phenylenediamine molecule was attached to the 6-position of β-cyclodextrin. 300 MHz $^1$H spectrum showed all the peaks of β-cyclodextrin and multiplets of aromatic peaks of o-phenylenediamino moiety at 6.3–6.6 ppm. $^{13}$C NMR spectrum showed all the normal peaks of β-cyclodextrin at 60.4, 72.0, 72.5, 73.5, 81.7 and 102.4; the peaks for the substituted glucose of cyclodextrin at 45.3, 70.0, 81.0, 84.5 and 101.6 and the six peaks for the o-phenylenediamino moiety at 111.1, 114.8, 117.6, 118.1, 135.6 and 136.3

Mono-6-flavo-β-cyclodextrin (5). Reaction of 500 mg of 4 with 1.0 g of alloxan monohydrate in 20 ml 1N HCl for 30 minutes at 60° C. afforded the desired flavocyclodextrin. Cyclodextrin derivatives were precipitated from the reaction mixture and recrystallized from a minimum amount of water. The crystals were further purified by C$^{18}$-HPLC to give pure 6-flavocyclodextrin. 300 MHz $^1$H NMR spectrum of the purified product showed all the signals for β-cyclodextrin and the aromatic signals of the flavin moiety at δ 7.6, 7.9, 8.09 and N-3 at δ 11.25. $^{13}$C NMR spectrum showed all the normal peaks of β-cyclodextrin at 60.2, 72.1, 72.6, 73.0, 81.8, 102.0 ppm from TMS; the peaks for the substitute glucose unit of β-cyclodextrin at 46.5, 66.9, 71.5–75, 84.6 and 102.8 (which match well with the $^{13}$C chemical shifts for the ribityl group of riboflavin) and 10 signals for flavin at 117.8, 125.9, 131.4, 134.1, 134.3, 134.8, 138.6, 150.7, 155.5, 159.7.

Figure 2:
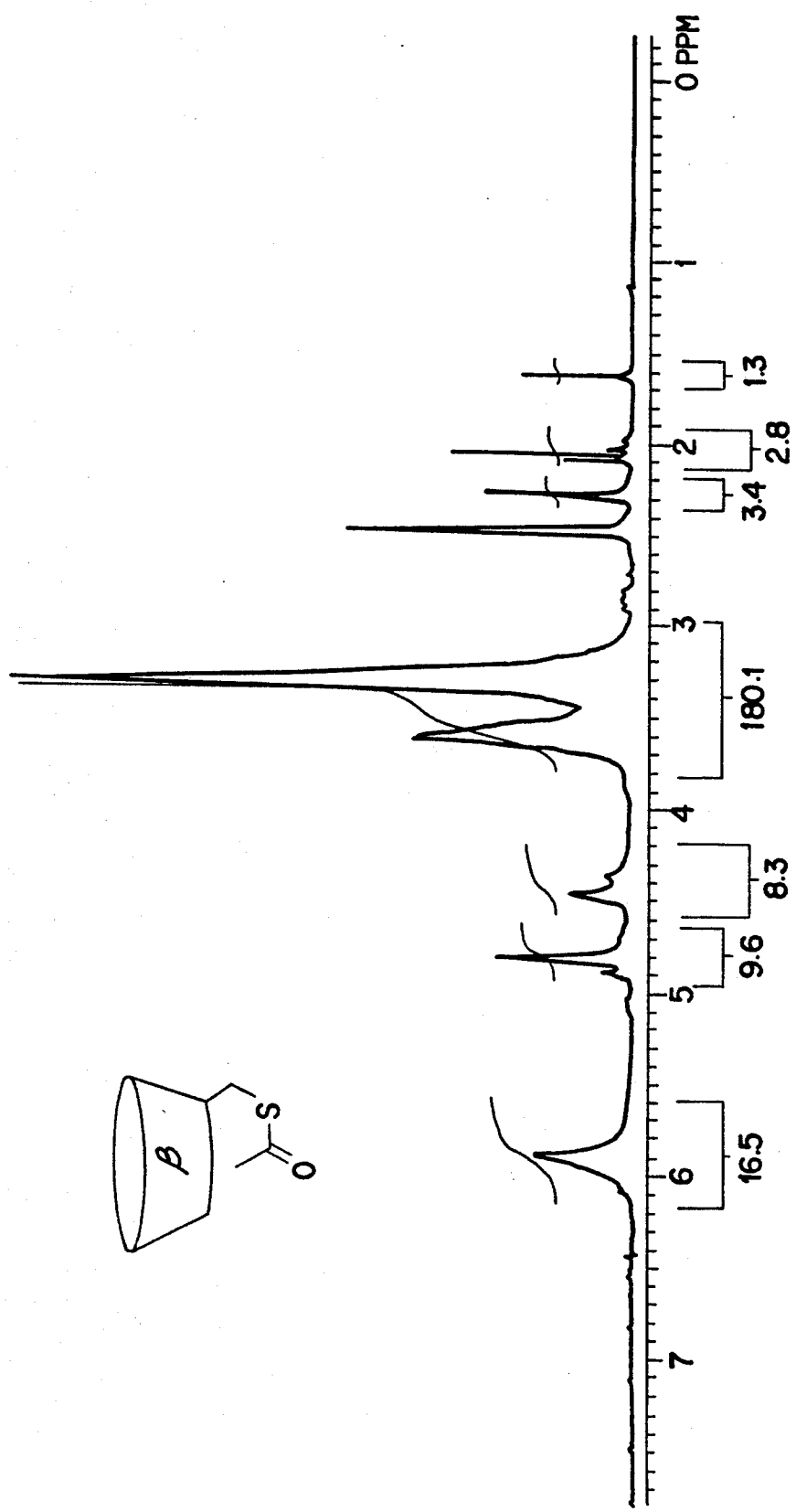
FIG. 2 shows a $^1$H NMR spectrum of structure 3 in Example 1.
Figure 3:
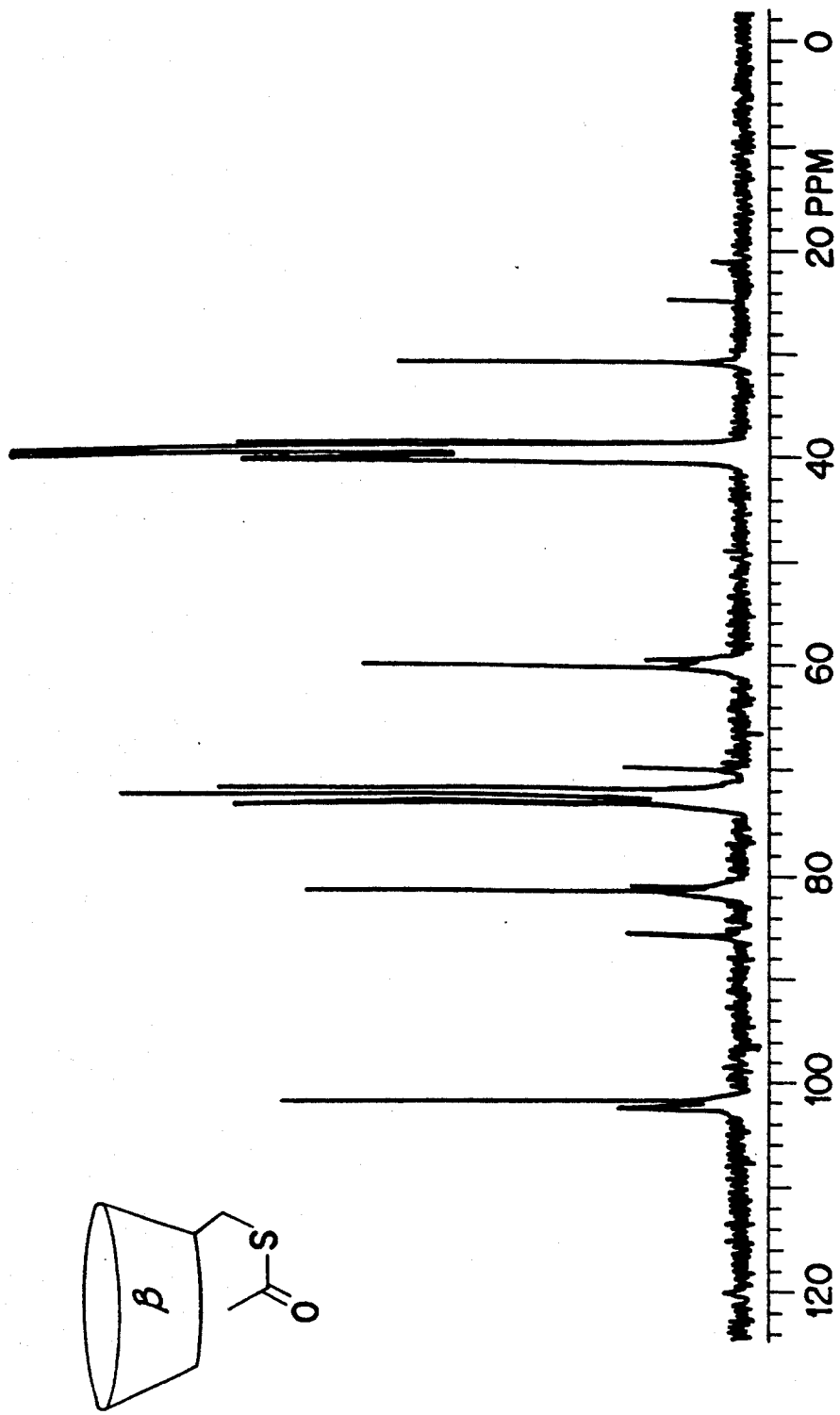
FIG. 3 shows a $^{13}$C NMR spectrum of structure 3 in Example 1.

FIGS. 2 and 3 are NMR spectra in $^1$H and $^{13}$C, respectively, of 3.

Figure 4:
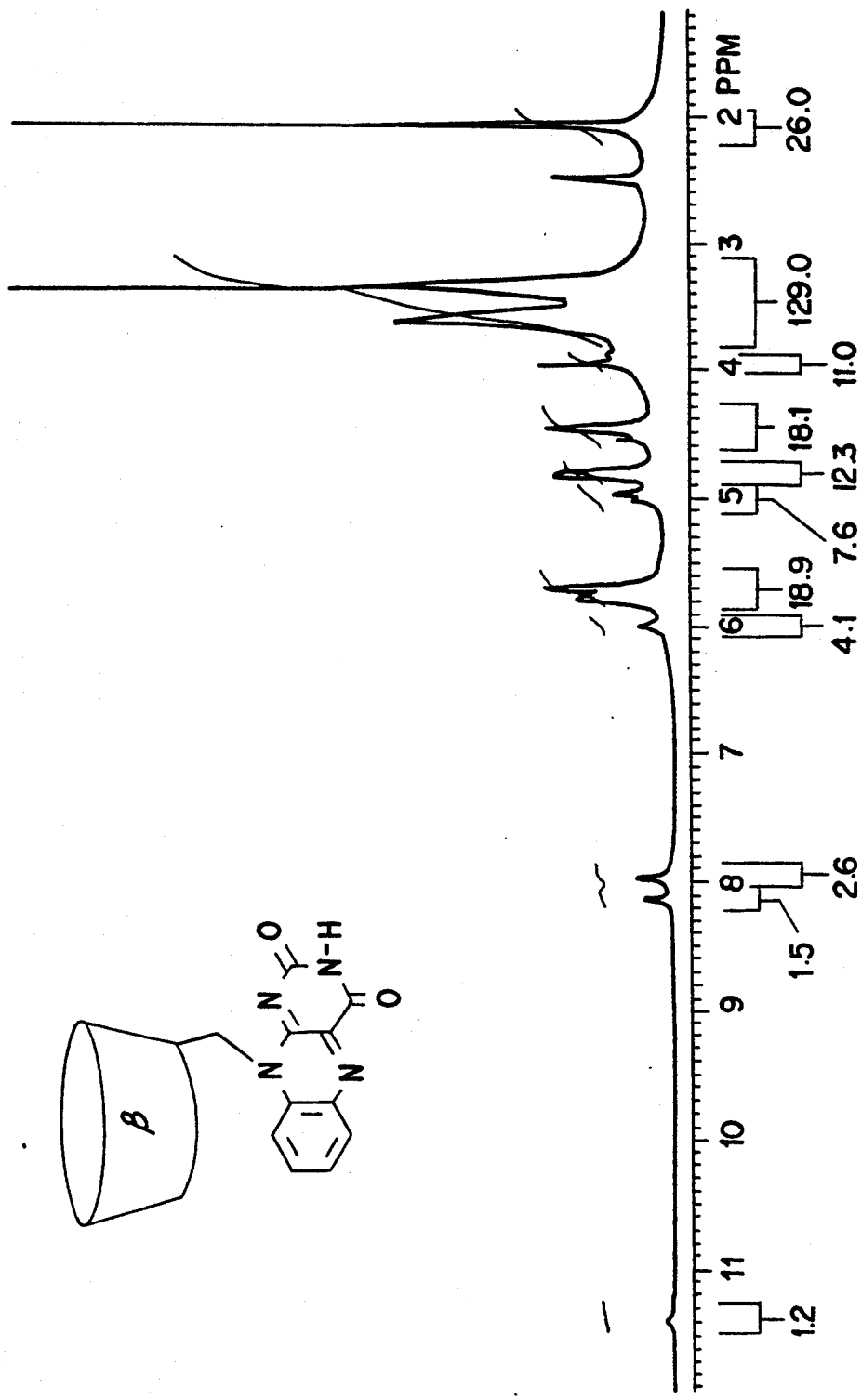
FIG. 4 shows a $^1$H NMR spectrum of structure 4 in Example 1.
Figure 5:
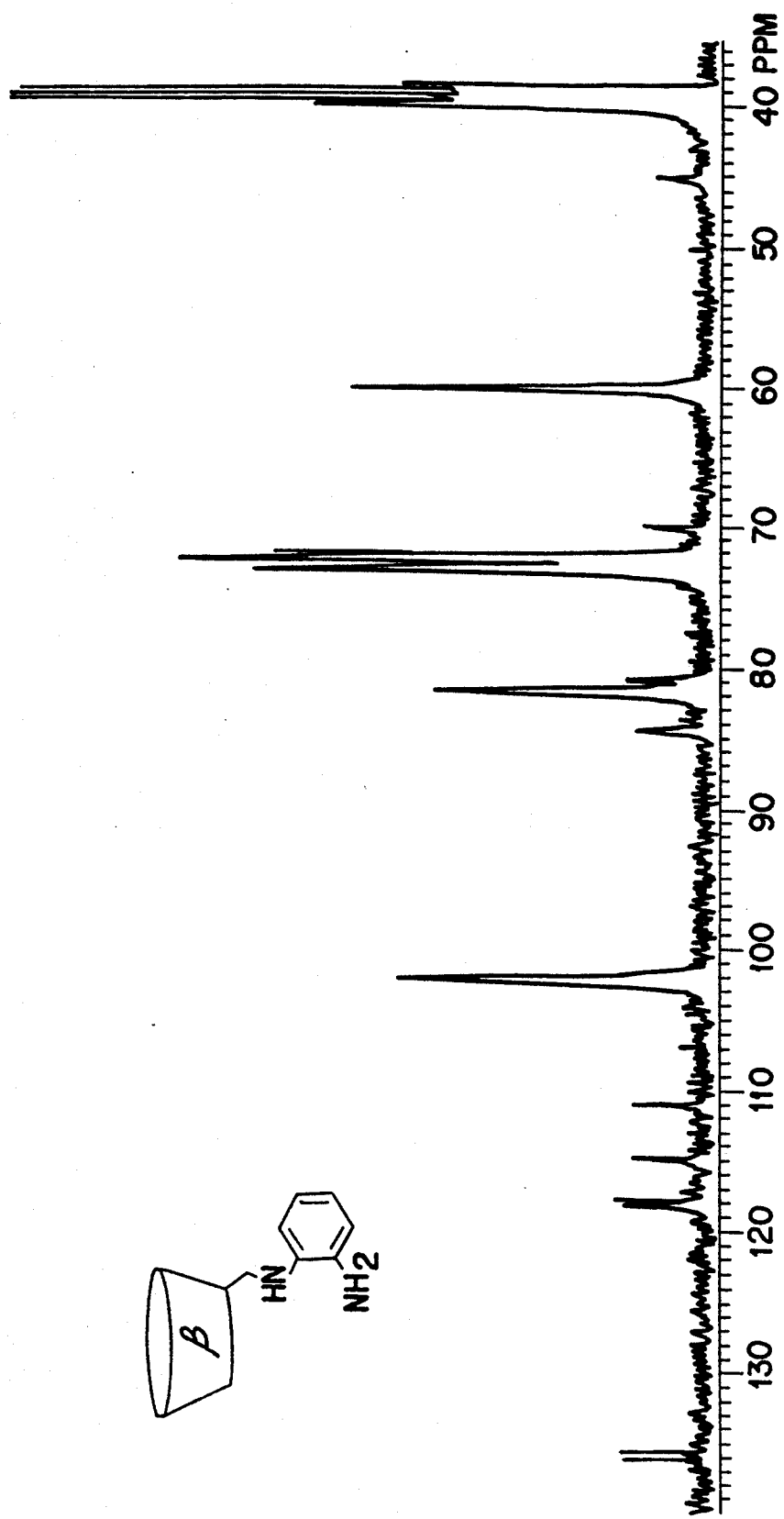
FIG. 5 shows a $^{13}$C NMR spectrum of structure 4 in Example 1.

FIGS. 4 and 5 are NMR spectra in $^1$H and $^{13}$C, respectively, of 4.

Figure 6:
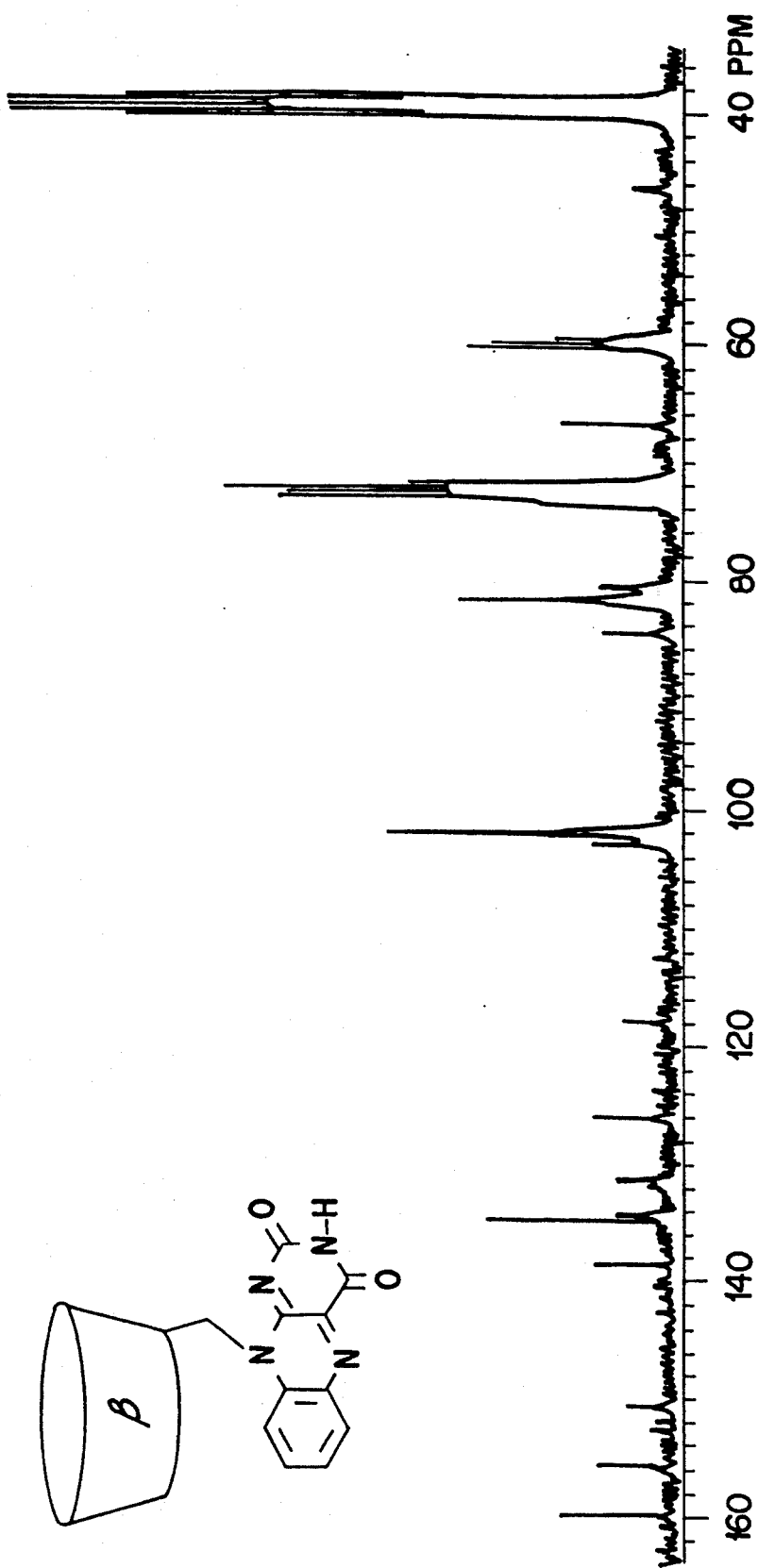
FIG. 6 shows a $^{13}$C NMR spectrum of structure 5 in Example 1.
Figure 7:
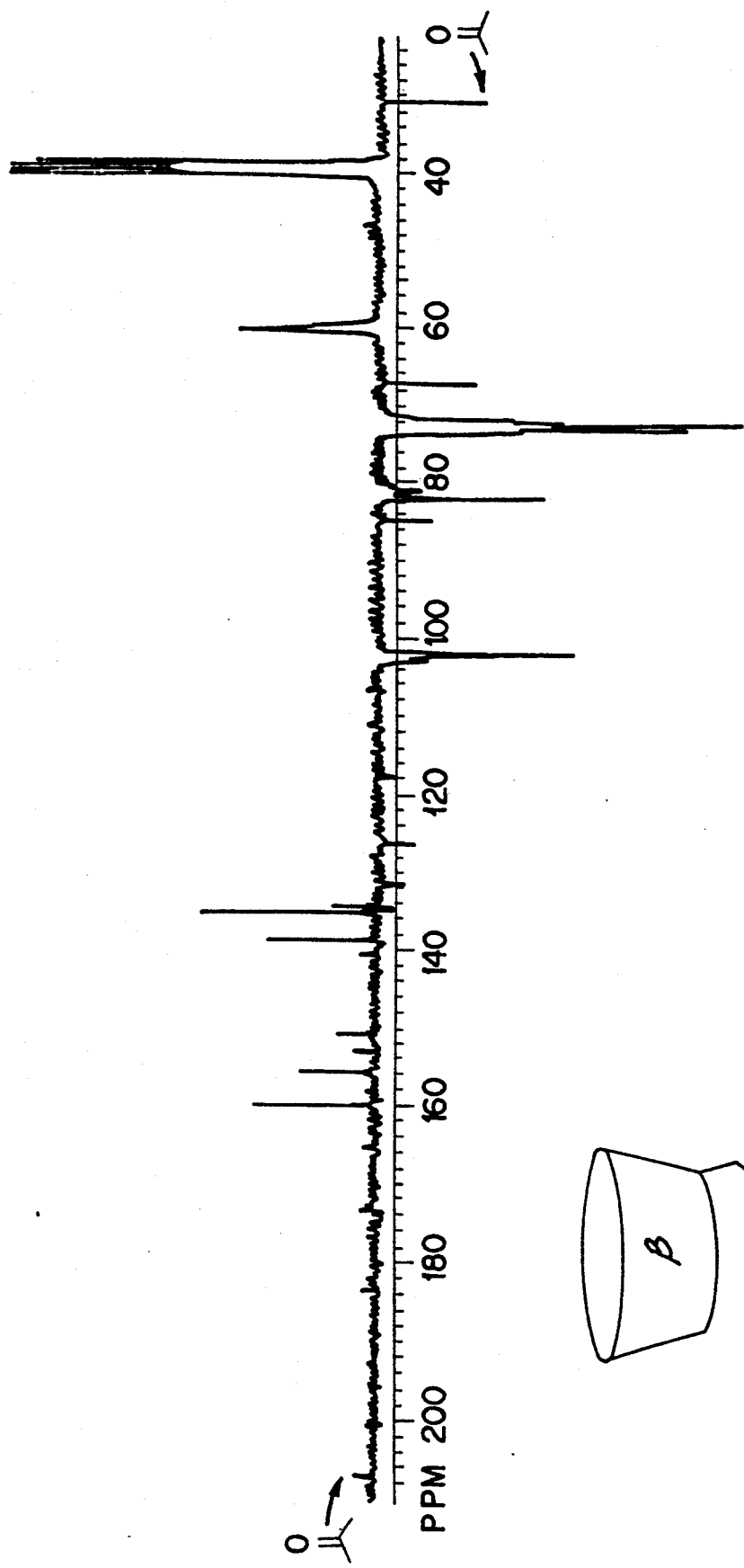
FIG. 7 shows a $^{13}$C(APT) NMR spectrum of structure 5 in Example 1.

FIGS. 6 and 7 are NMR spectra in $^{13}$C and $^{13}$C(APT), respectively, of 5.

EXAMPLE 2

Synthesis of Mono-2-flavo-β-cyclodextrin 12

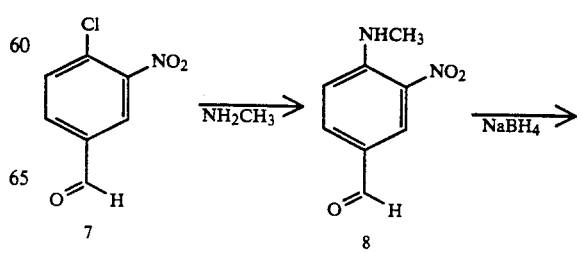

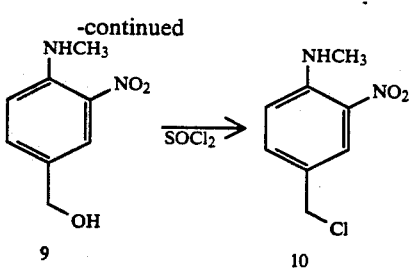

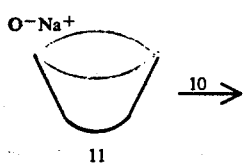

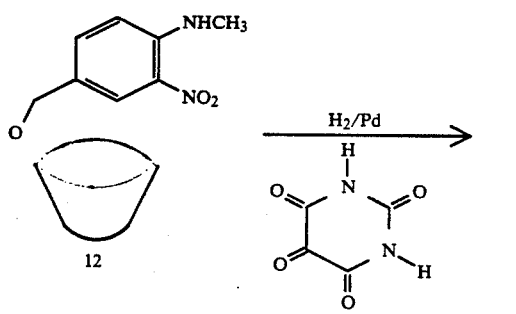

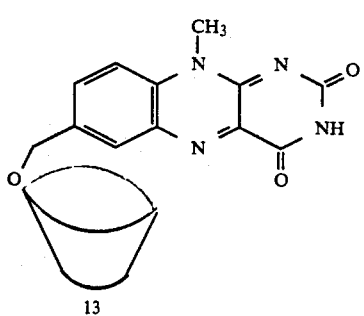

4-Methylamino-3-nitro-benzylaldehyde (8). To a 30 ml ethanol solution containing 4.0 g (22 mmol) of 4-chloro-3-nitrobenzylaldehyde (7), 50 ml aqueous methylamine solution (40%) was added and the solution was then refluxed for three hours; the precipitate was collected after being cooled in a refrigerator overnight. The precipitate was then washed with water and then dissolved in 400 ml 1N HCl and stirred overnight. The precipitate was filtered, washed with water to yield 3.2 g (81%) of yellow 8, mp:173.5°-175.0° C. $^1$H NMR:(CDCl$_3$) δ 9.78 (s, 1H, CH=O), 8.64 (d, 1H, J=1.9 Hz, H-2), 7.97 (dd, 1H, J=9, 1.5 Hz, H-5) H(H-5), 6.94(d, 1H, J=9 Hz, H-5), 3.11(d, 3H, J=5.2 Hz, CH$_3$), 8.54 (broad, 1H, NH). Anal. Calcd for C$_8$H$_8$N$_2$O$_3$:C, 53.33; H, 4.48; N, 15.55; O, 26.64; found: C, 53.45; H, 4.55; N, 15.58; O, 26.42.

4-Methylamino-3-nitro-benzylalcohol (9). 0.32 g (8.3 mmol) of sodium borohydride was added to 20 ml absolute alcohol solution containing 3.0 g (16.6 mmol) of 8. The suspension was stirred for 3 hours. The solution was then cooled in an ice/water bath, and 8.5 ml 2N HCl was added dropwise to the solution to decompose unreacted sodium borohydride. The pH of the solution was adjusted to 10 by adding about 10 ml of concentrated ammonium hydroxide and then extracted with 60 ml chloroform three times. After being dried over magnesium sulfate and evaporated, the residue was recrystallized from water to yield 1.7 g (56%) of orange 9. mp:126°-127° C.

$^1$H NMR: (DMSO-d$_6$) δ 8.15 (s, 1H, NH), 8.01(s, 1H, H-2), 7.50 (d, 1H, J=8.6 Hz, H-5), 6.97p, (d, 1H, J=8.8 Hz, H-6), 5.22(s, 1H, OH), 4.41(s, 2H, CH$_2$), 2.96(d, 3H, J=4.7 Hz, CH$_3$). $^{13}$C NMR:(DMSO-d$_6$) δ 145.15, 135.70, 130.29, 129.30, 123.44, 114.20, 61.70, 29.69. Anal. Calcd for C$_8$H$_4$N$_2$O$_3$:C, 52.74; H, 5.53; N, 15.38; O, 26.35; found: C, 53.02; H, 5.52; N, 15.48; O, 25.98.

4-Methylamino-3-nitrobenzylchloride (10). 1.0 g (5.5 mmol) of 9 was dissolved in 25 ml thionylchloride at −78° C. cooled with dry ice/acetone bath. After it dissolved completely, the dry ice/acetone bath was removed and the reaction mixture allowed to warm up to room temperature and kept at room temperature for additional 1 hour. Thionylchloride was evaporated under vacuum at room temperature and the residue was washed with 5 ml cold diethylether and recrystallized from diethylether to yield 0.6 g (55%) of 10. Yellow, mp: 126°-128° C. $^1$H NMR: (DMSO-d$_6$): δ 82.9 (s, 1H, NH), 8.15 (d, 1H, J=2.2 Hz, H-2), 7.60p, 1H, (dd, 1H, J=8.9, 2.2 Hz, H-6), 7.01 (d, 1H, J=9.0 Hz, H-5), 4.76 (s, 3H, CH$_2$), 2.95 (s, 3H, CH$_3$). Anal. Calcd for C$_8$H$_9$N$_2$O$_2$Cl: C, 47.89; H, 4.52; Cl, 17.67; N, 14.00; O, 15.95. found: C, 47.78; H, 4.49; Cl, 17.78; N, 13.82; O, 16.13.

2-O-(4-Methylamino-3-nitro)benzyl-β-cyclodextrin (12). To a solution of 1.0 g (0.88 mmol) of β-cyclodextrin in 40 ml DMF was added 35 mg (60% in oil; 0.88 mmol) of NaH and the mixture was stirred overnight until the solution became clear (11). This solution was added dropwise to a 5 ml DMF solution containing 0.173 g (0.88 mmol) of 10 and allowed to stand at room temperature for 30 minutes. β-cyclodextrin and its derivatives were precipitated out by addition of 500 ml acetone. The precipitate was filtered and washed with 100 ml acetone to remove all the unreacted reagent and to give 1.0 g crude product containing only 12 and unreacted β-cyclodextrin as indicated by TLC. The mixture was separated by Sephadex chromatography to furnish 0.4 g (35%) of 12, yellow, Rf=0.55, $^1$H NMR (DMSO-d$_6$) δ 8.21 (1H, d, J=4.7 HZ, N-H), 8.07 (1H, s, H-2), 7.60 (1H, d, J$_{5,6}$=9.0 Hz, H-6), 7.01 (1H, d, J$_{5,6}$=9.0 Hz, H-5), 6.0-3.2 (protons of β-cyclodextrin), 2.96 (3H, d, J=4.7 Hz, CH$_3$) Anal. Calcd for C$_{50}$H$_{78}$O$_{37}$N$_2$.5H$_2$O: C, 42.68; H, 6.45; N, 1.99; O, 48.88; found: C, 42.83; H, 6.44; N, 1.93; O, 48.80.

Mono-2-flavo-β-cyclodextrin (13). 0.46 g of 12 was hydrogenated in 80 ml methanol catalyzed by 0.2 g Pd/C (10%) to yield a colorless solution. The solvent was evaporated under vacuum below 40° C. and the residue was washed with 160 ml of acetone. The precipitate was collected and dried. The crude product was condensed with 5 g alloxan in 5 ml 1N HCl at refluxing acetone for 30 minutes. After addition of 100 ml of acetone, the precipitate was collected and was applied to a Sephadex (G-25-100) column to yield 30 mg (24%) of 13, yellow, mp.>250° C., Rf=0.28, $^1$H NMR (DMSO-d$_6$) δ 8.15(m, 1H), 7.98(m, 2H), 11.41(s, 1H, N$_3$-H) and the normal β-cyclodextrin peaks.

$^{13}$C MNR (DMSO-d$_6$): δ flavin: 160.2, 156.1, 151.5, 139.1, 136.5, 135.0, 134.7, 133.2, 130.5, 117.0, 32.0(CH$_3$) and six peaks for the normal β-cyclodextrin at: 102.0, 81.60, 73.10, 72.41, 72.05, 60.00; C-2': 80.01, C-1': 100.02.

Figure 8:
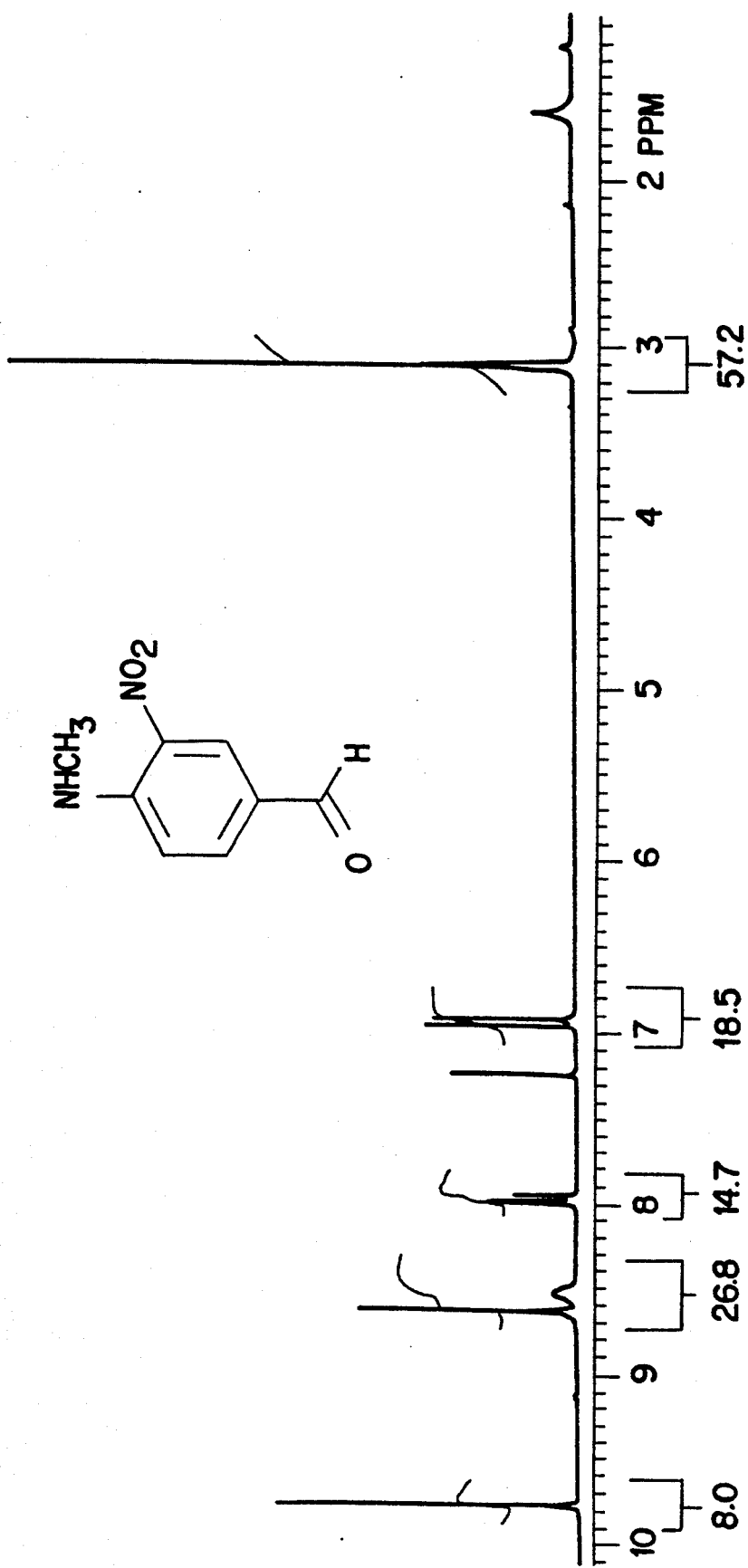
FIG. 8 shows a $^1$H NMR spectrum in CDCl$_3$ of structure 8 of Example 2.

FIG. 8 is a $^1$H NMR spectrum in CD Cl$_3$ of 8.

Figure 9:
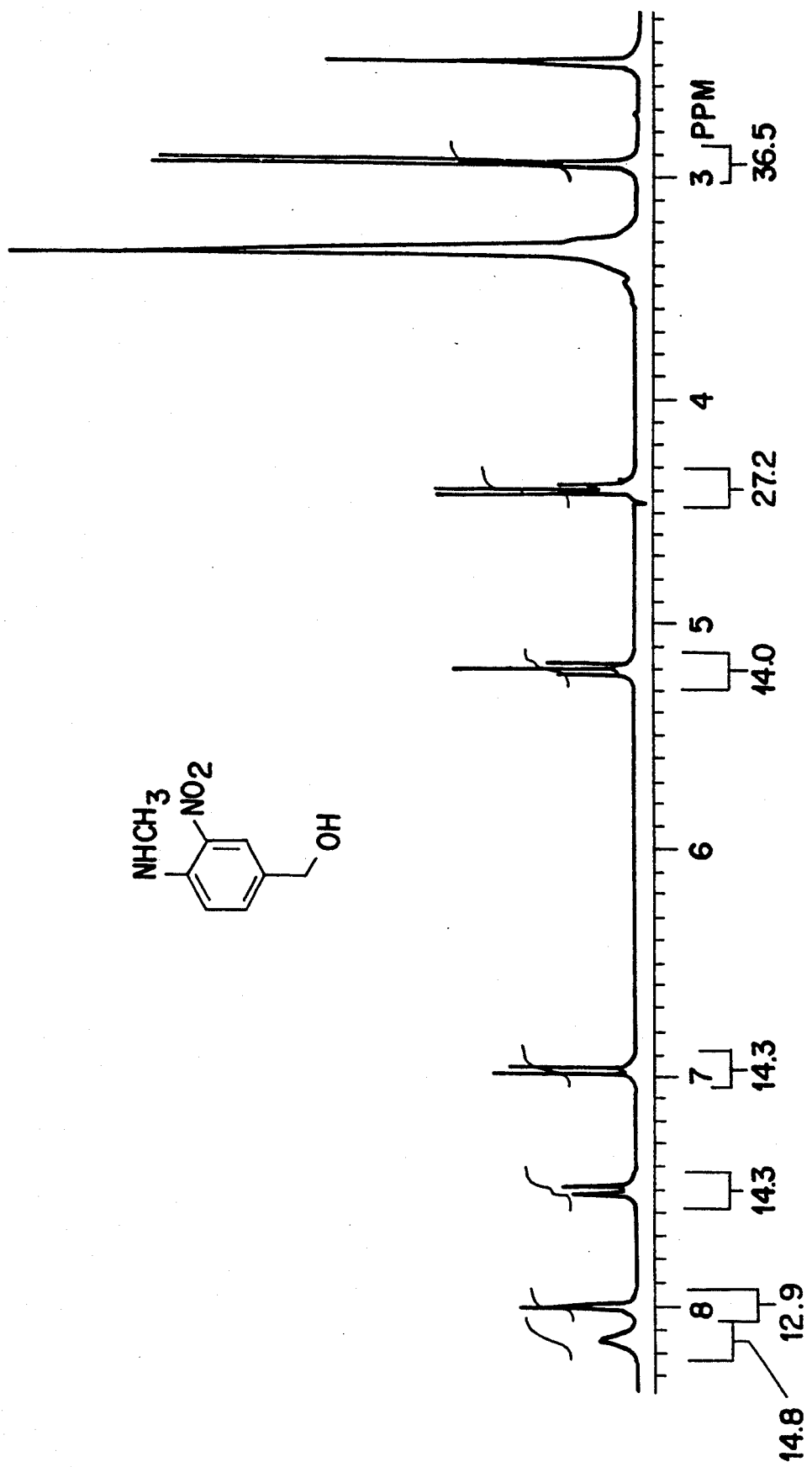
FIG. 9 shows a $^1$H NMR spectrum in DMSO-d6 of structure 9 of Example 2.
Figure 10:
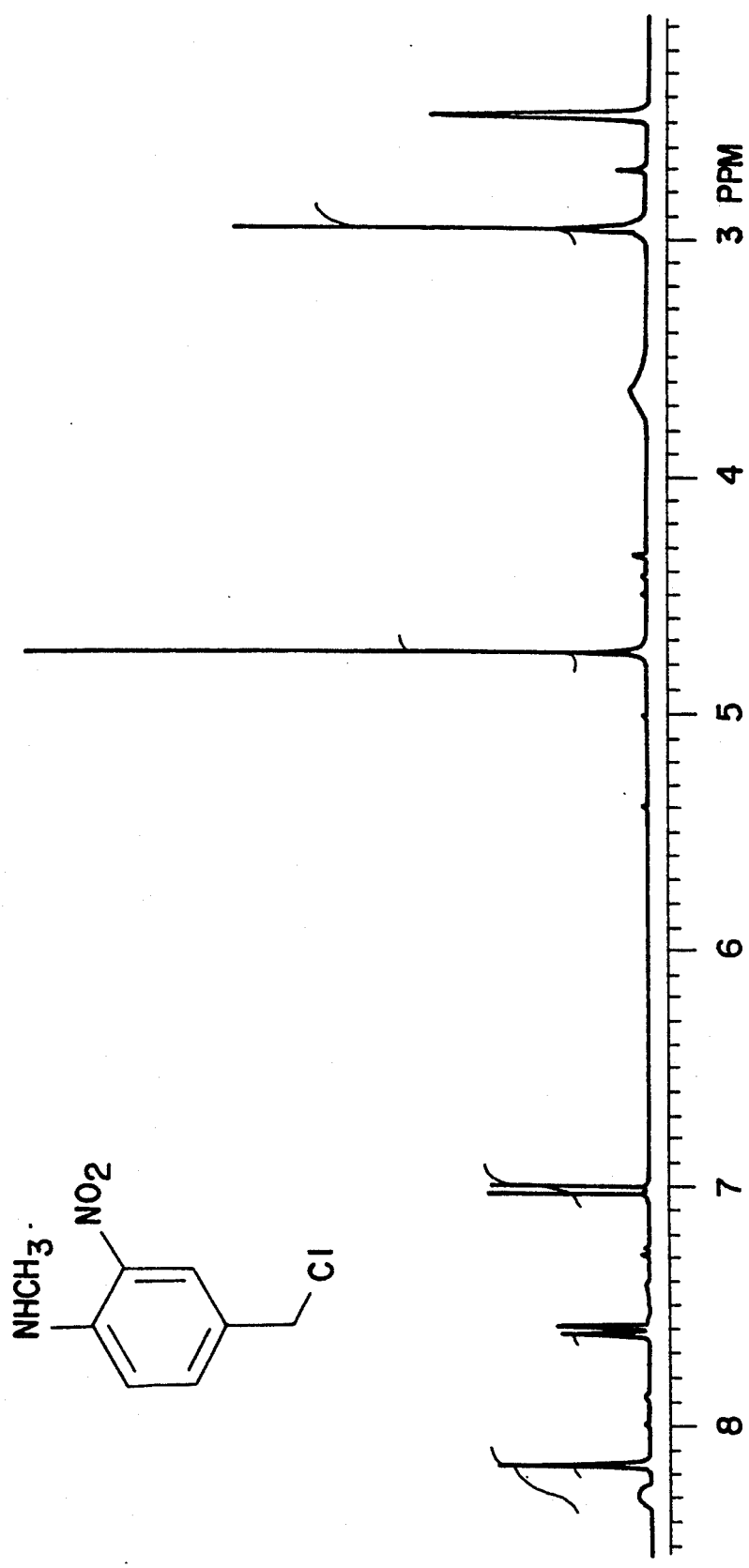
FIG. 10 shows a $^1$H NMR spectrum in DMSO-d6 of structure 10 of Example 2.
Figure 11:
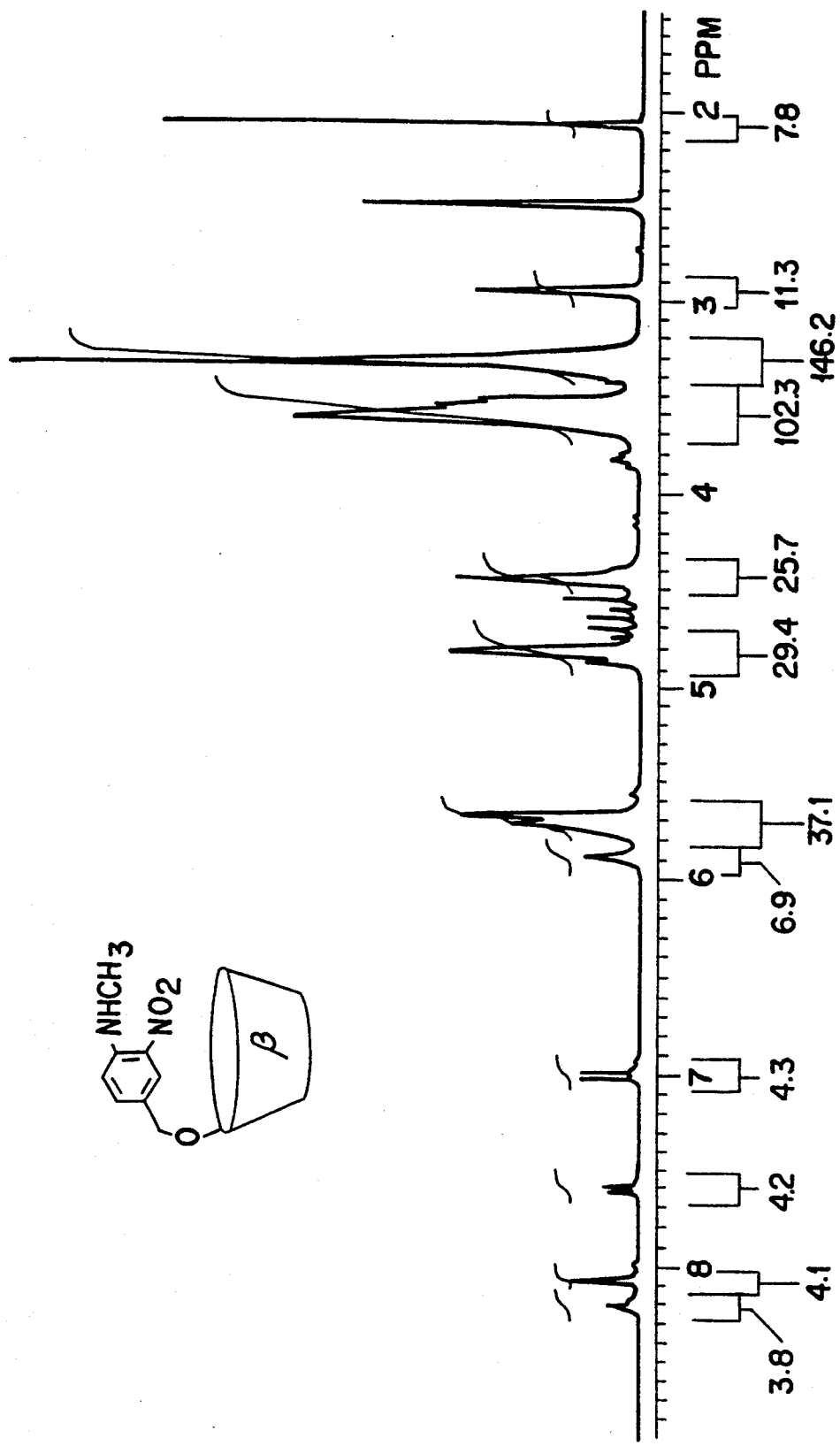
FIG. 11 shows a $^1$H NMR spectrum in DMSO-d6 of structure 12 of Example 2.
Figure 12:
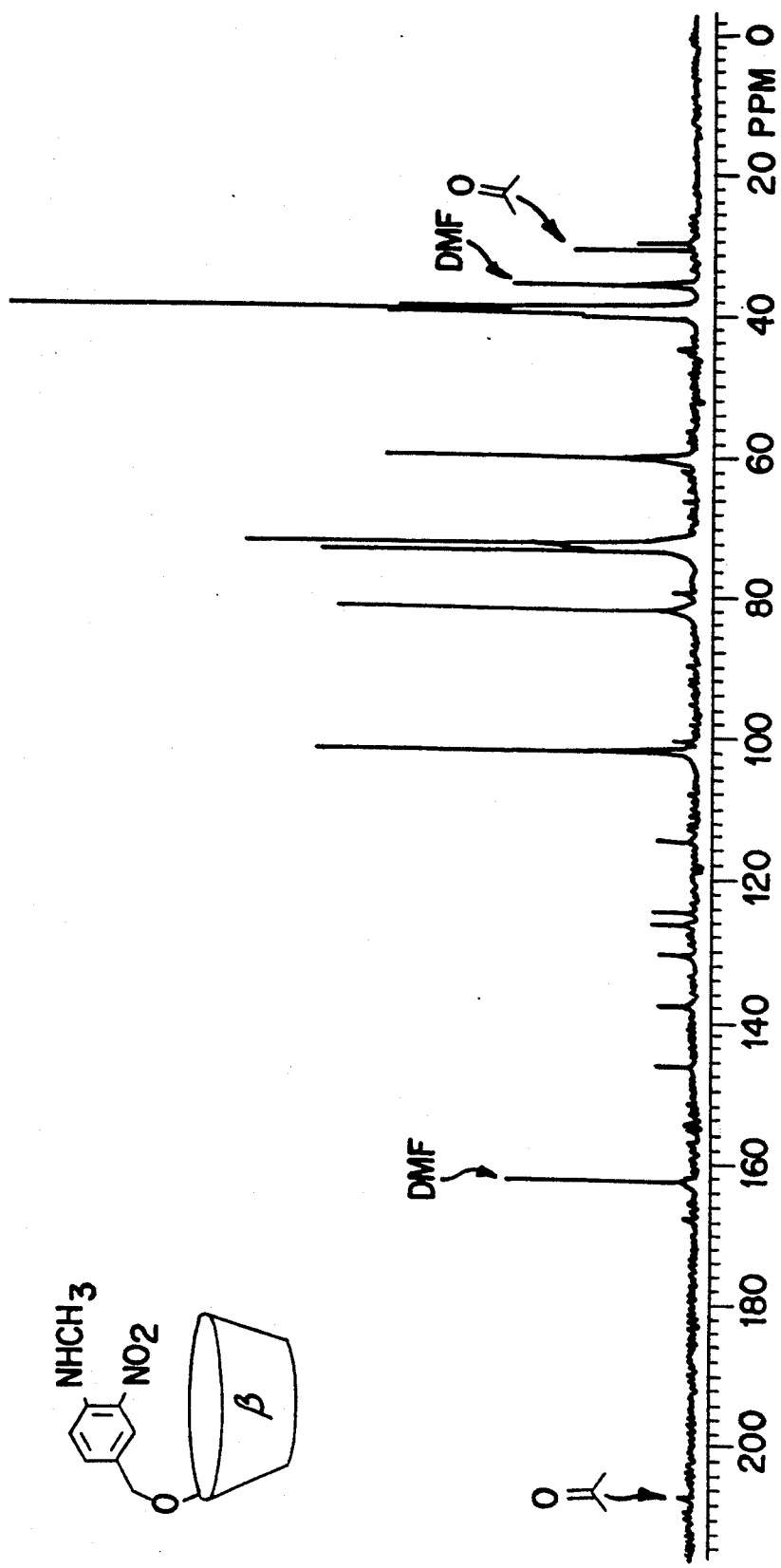
FIG. 12 shows a $^{13}$C NMR spectrum in DMSO-d6 of structure 12 of Example 2.

FIG. 9 is a $^1$H NMR spectrum in DMSO-d$_6$ of 9.
FIG. 10 is a $^1$H NMR spectrum in DMSO-d$_6$ of 10.
FIG. 11 is a $^1$H NMR spectrum in DMSO-d$_6$ of 12, and FIG. 12 is a $^{13}$C NMR spectrum in DMSO-d$_6$ of the same molecule.

Figure 13:
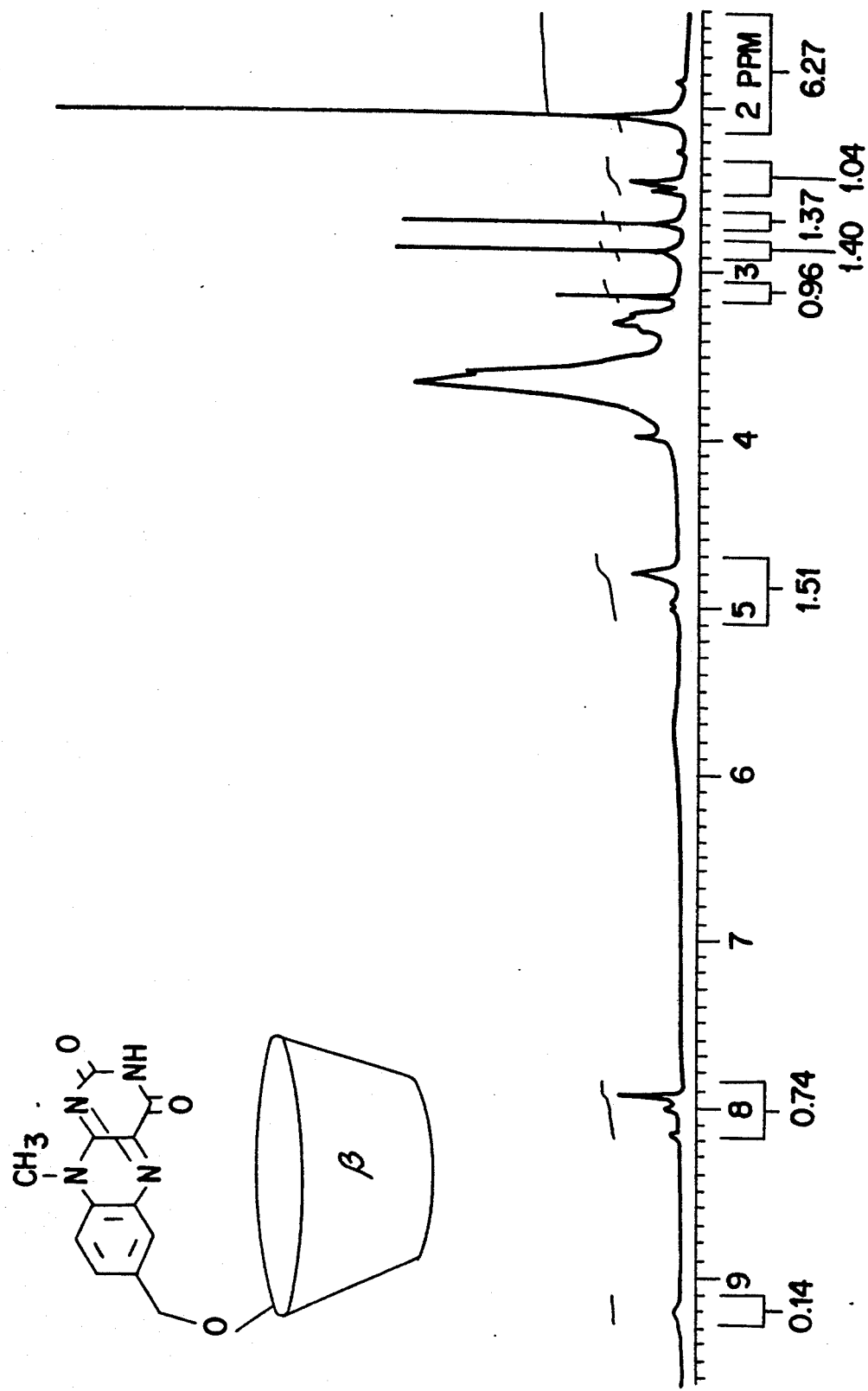
FIG. 13 shows a $^1$H NMR spectrum in DMSO-d6 of structure 13 of Example 2.
Figure 14:
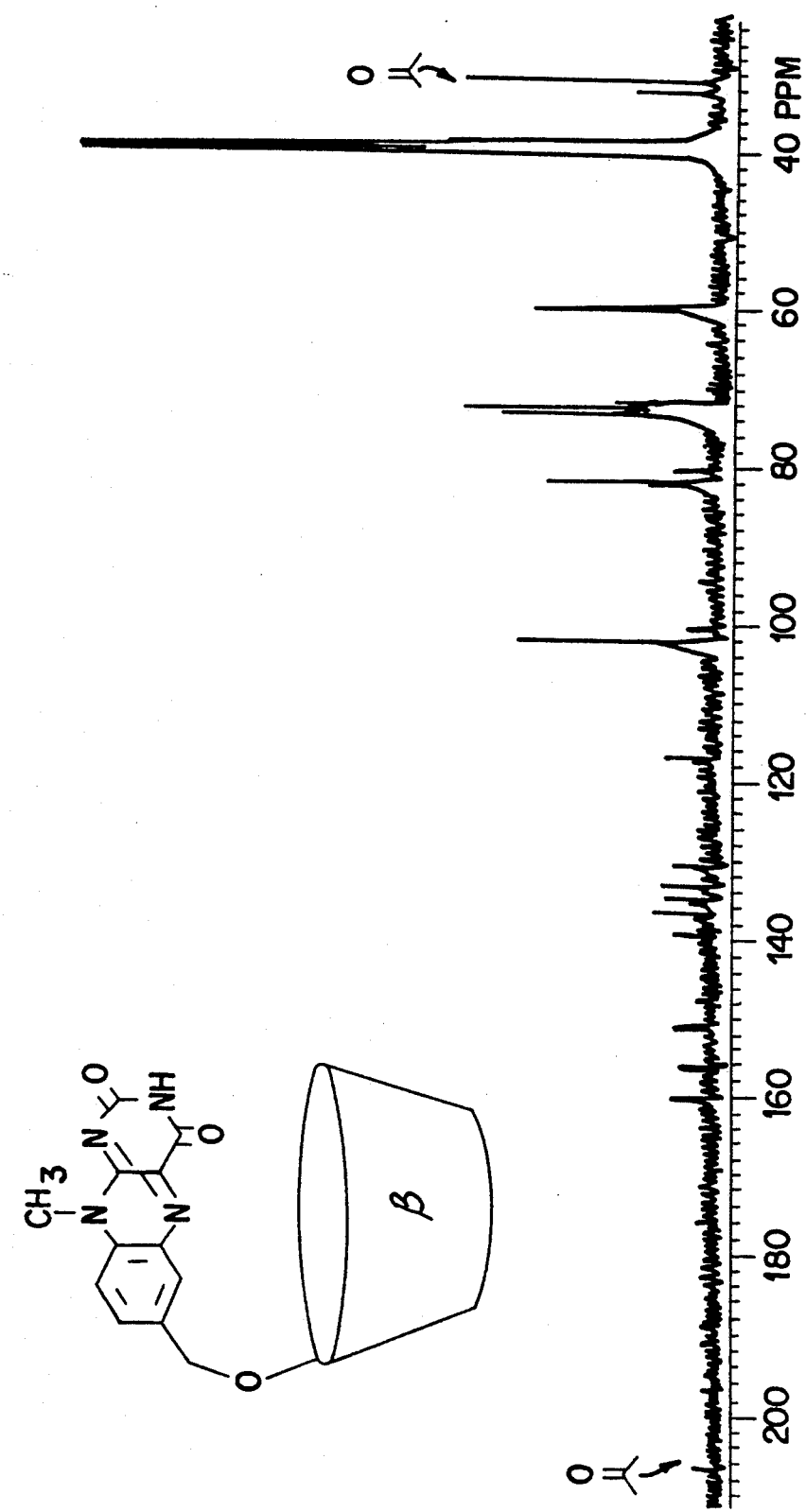
FIG. 14 shows a $^{13}$C NMR spectrum in DMSO-d6 of structure 13 of Example 2.

FIGS. 13 and 14 are $^1$H and $^{13}$C NMR spectra in DMSO-d$_6$ of 13.

EXAMPLE 3

Synthesis of Mono-2-flavo-α-cyclodextrin

The α-cyclodextrin analogue of the 2-flavo-β-cyclodextrin of Example 2 was synthesized by the same synthetic route.

2-O-(4-Methylamino-3-nitro)benzyl-α-cyclodextrin (12). To a solution containing 3.9 g (4.0 mmol) α-cyclodextrin in 40 ml DMF / 40 ml DMSO was added 160 mg (60% in oil; 4.0 mmol) of NaH and the mixture was stirred for 5 hours. 5 ml DMF solution containing 0.80 g (4.0 mmol) of 10 was added to the solution and it was allowed to stand at room temperature for 1 hour. The cyclodextrin derivatives were precipitated out by addition of 1L acetone. The precipitate was collected and washed with acetone to give 4.0 g crude products containing only 12 and α-cyclodextrin indicated by TLC. 50 mg of 12 was isolated from 300 mg crude product by Sephadex chromatography. Orange, Rf: 0.56, $^1$H NMR (D$_2$O) δ

$^{13}$C NMR (D$_2$O) δ 31.2(CH$_3$—), 73.4(CH$_2$), 61.2(C6), 72.5, 72.8, 74.3 (C2, 3, 5), 82.2 (C4), 102.2 (C1), 79.8 (C2'), 100.4 (C1'), 115.5, 124.9, 127.5, 130.9, 138.6, 147.5 for aromatic carbons. APT $^{13}$C NMR show: C or CH2 are δ 61.2, 72.4, 124.9, 112.9, 129.5. CH or CH$_3$ are δ the rest of the peaks shown in the above $^{13}$C NMR.

Mono-2-flavo-α-cyclodextrin (13). 1.5 g of 12 was in 250 ml methanol catalyzed by 0.3 g Pd/C (5%) at room temperature for 24 hours until the solution was almost colorless and then filtered. The filtrate was evaporated and 20 ml acetone was added to the residue. The precipitate was then filtered and washed with acetone to give 1.5 g precipitate. 0.70 g of the precipitate was allowed to react with 2.8 g alloxan monohydrate in 10 ml 1N HCl for 40 minutes heated by boiling in an acetone bath. The solution was cooled with ice-water, and 200 ml acetone was added to precipitate the cyclodextrin derivatives. The precipitate was purified by Sephadex chromatography to yield 50 mg (40%) of 13, yellow, Rf: 0.24. $^1$H NMR(D$_2$O). It shows all the normal proton peaks for α-cyclodextrin and 7.22ppm(d, 1H, J=), and 7.38ppm(m, 2H) for flavin. $^{13}$C NMR(D$_2$O) δ33.0(CH$_3$), 60.3(C6), 71.5, 72.0, 73.3(C2, 3, 5), 81.2(C4), 101.4(C1), 79.6(C2'), 99.2(C1'), 117.3, 130.3, 133.1, 135.2, 136.4, 137.0, 137.6, 150.2, 157.6, 160.9 for flavin. APT 13C NMR show C or CH2 are δ 6 60.3, 133.1, 135.2, 136.4, 137.6, 150.2, 157.6, 160.9 CH or CH3 are all the rest of the peaks shown in the above $^{13}$C NMR.

Figure 15:
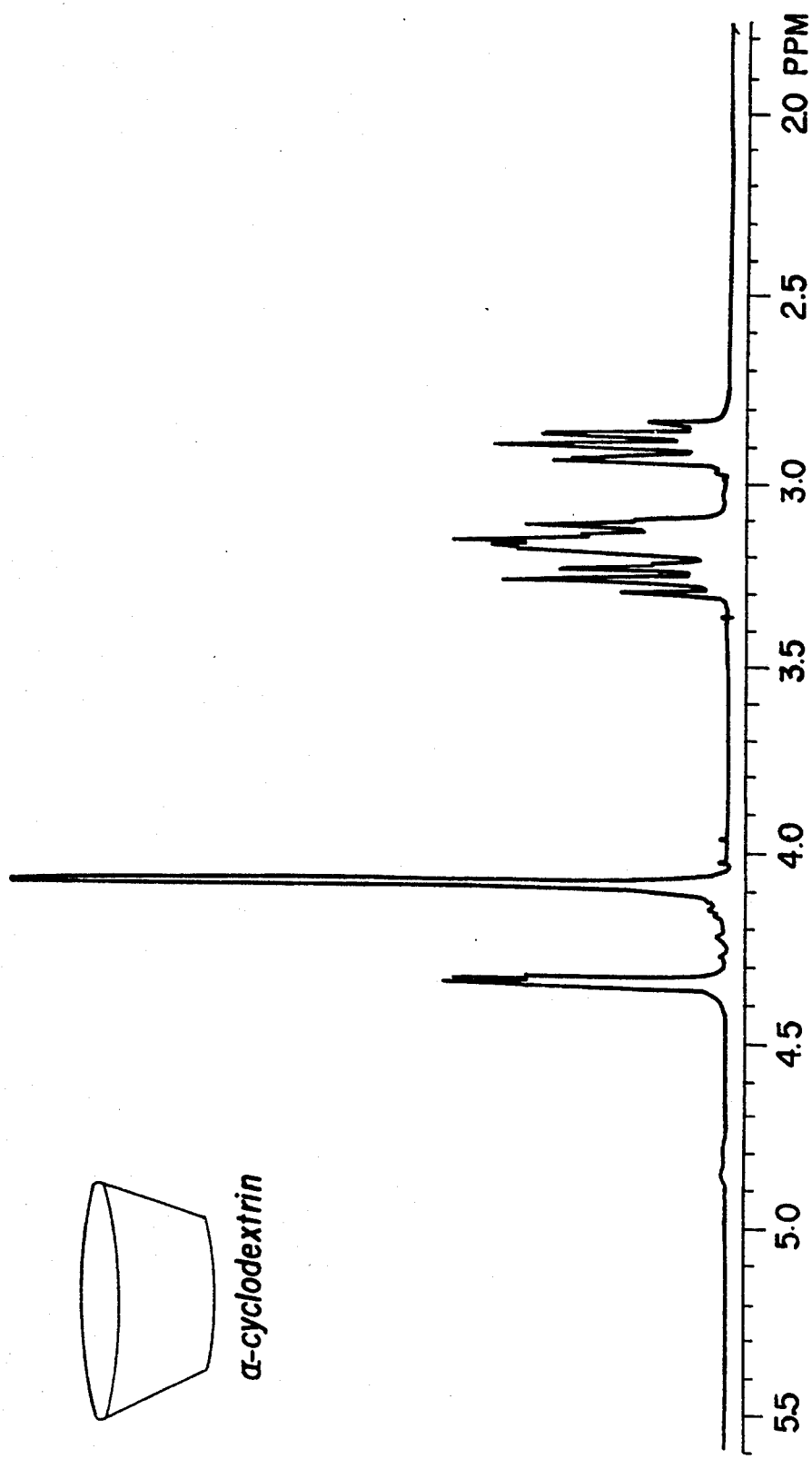
FIG. 15 shows a $^1$H NMR spectrum of β-cyclodextrin.
Figure 16:
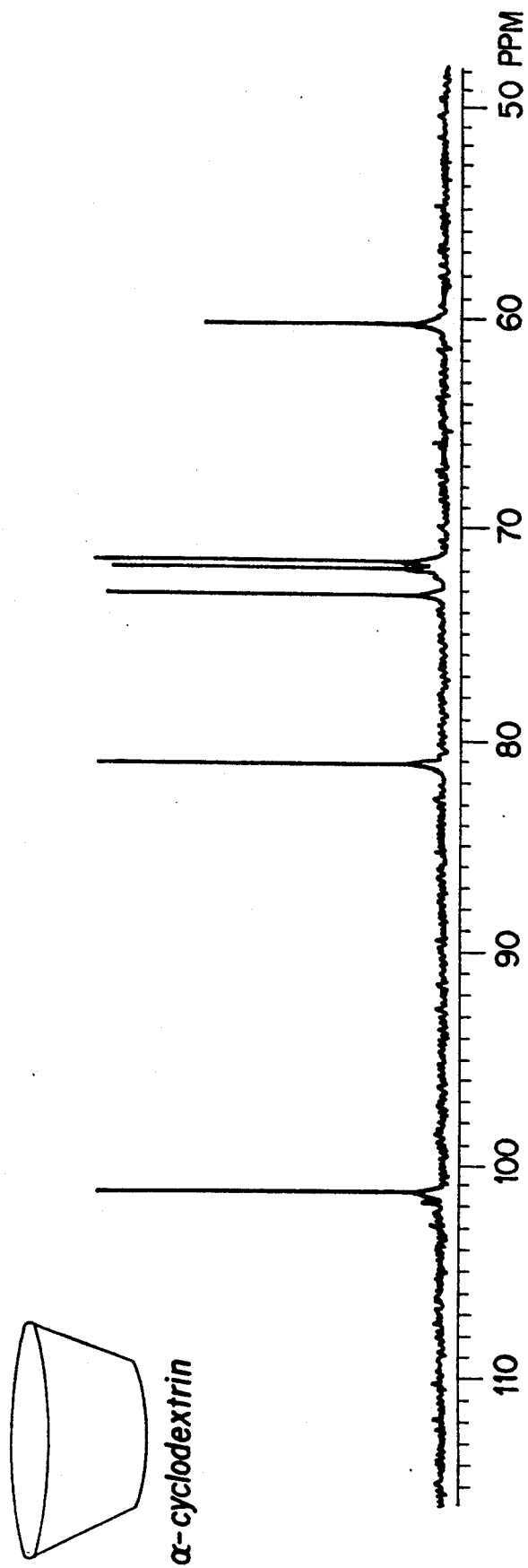
FIG. 16 shows a $^{13}$C NMR spectrum of α-cyclodextrin.

FIGS. 15 and 16 are the $^1$H and $^3$H NMR spectra, respectively, of the parent αCD (11).

Figure 17:
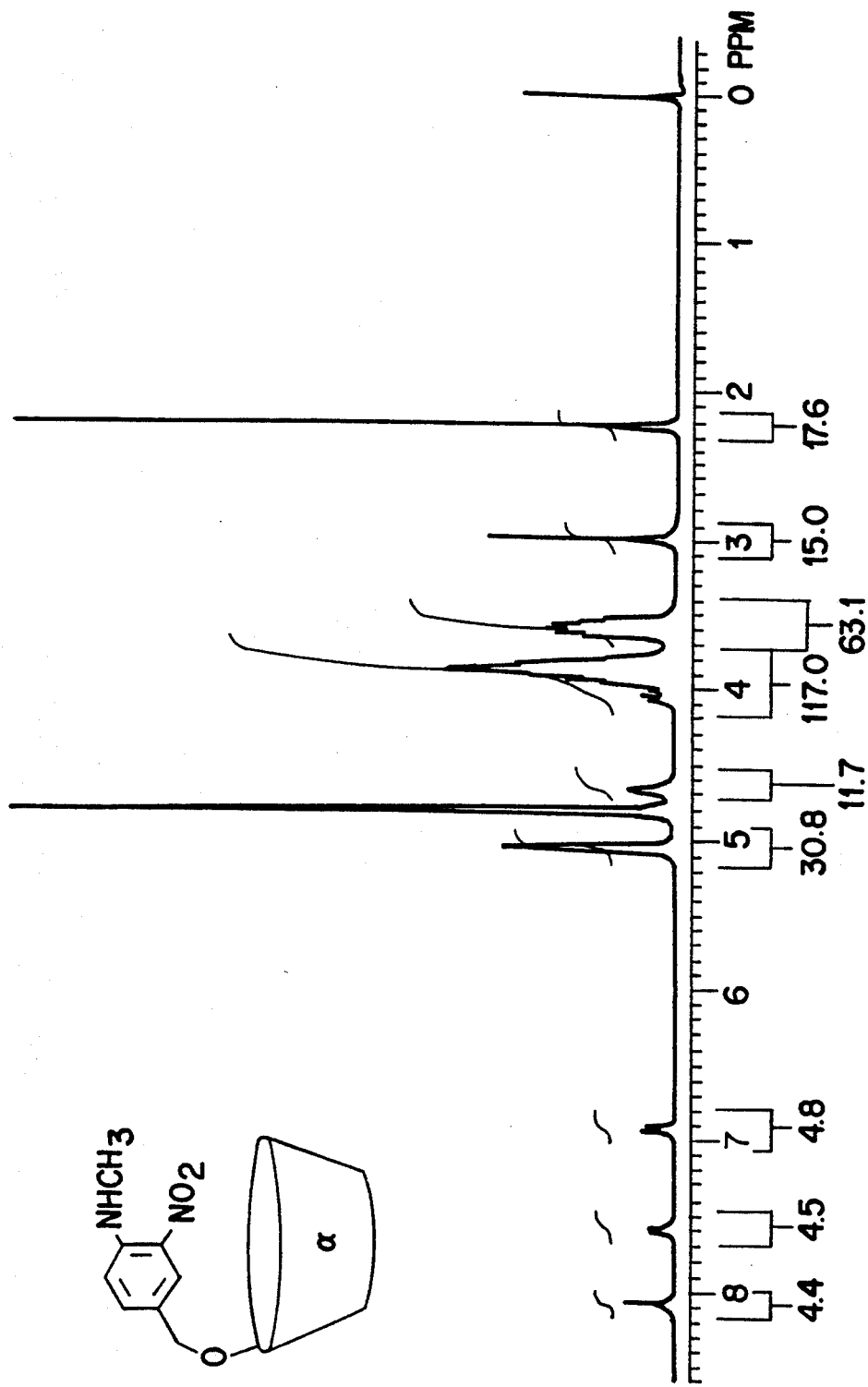
FIG. 17 shows a $^1$H NMR spectrum of the α-cyclodextrin analogue of structure 12 of Example 2.
Figure 18:
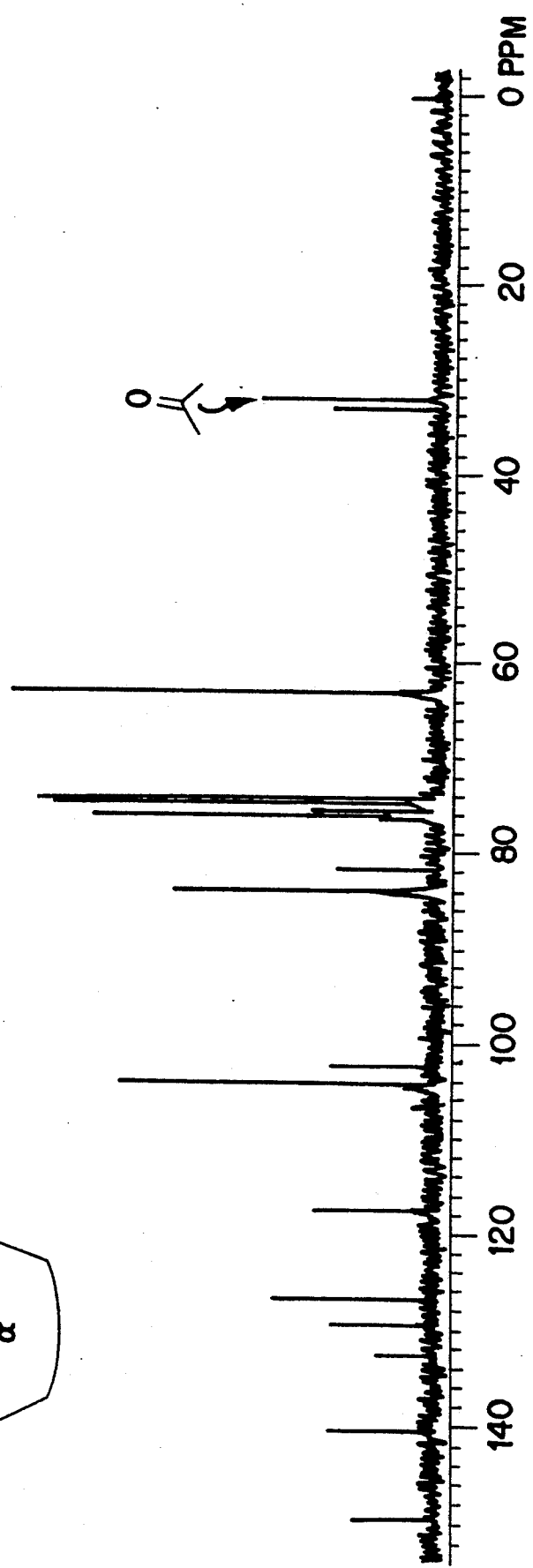
FIG. 18 shows a $^{13}$C NMR spectrum of the α-cyclodextgrin analogue of structure 12 of Example 2.
Figure 18:
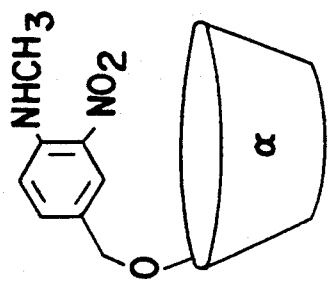

FIGS. 17 and 18 are the $^1$H and $^3$H NMR spectra, respectively, of the α-CD analogue of 12 of Example 2.

Figure 19:
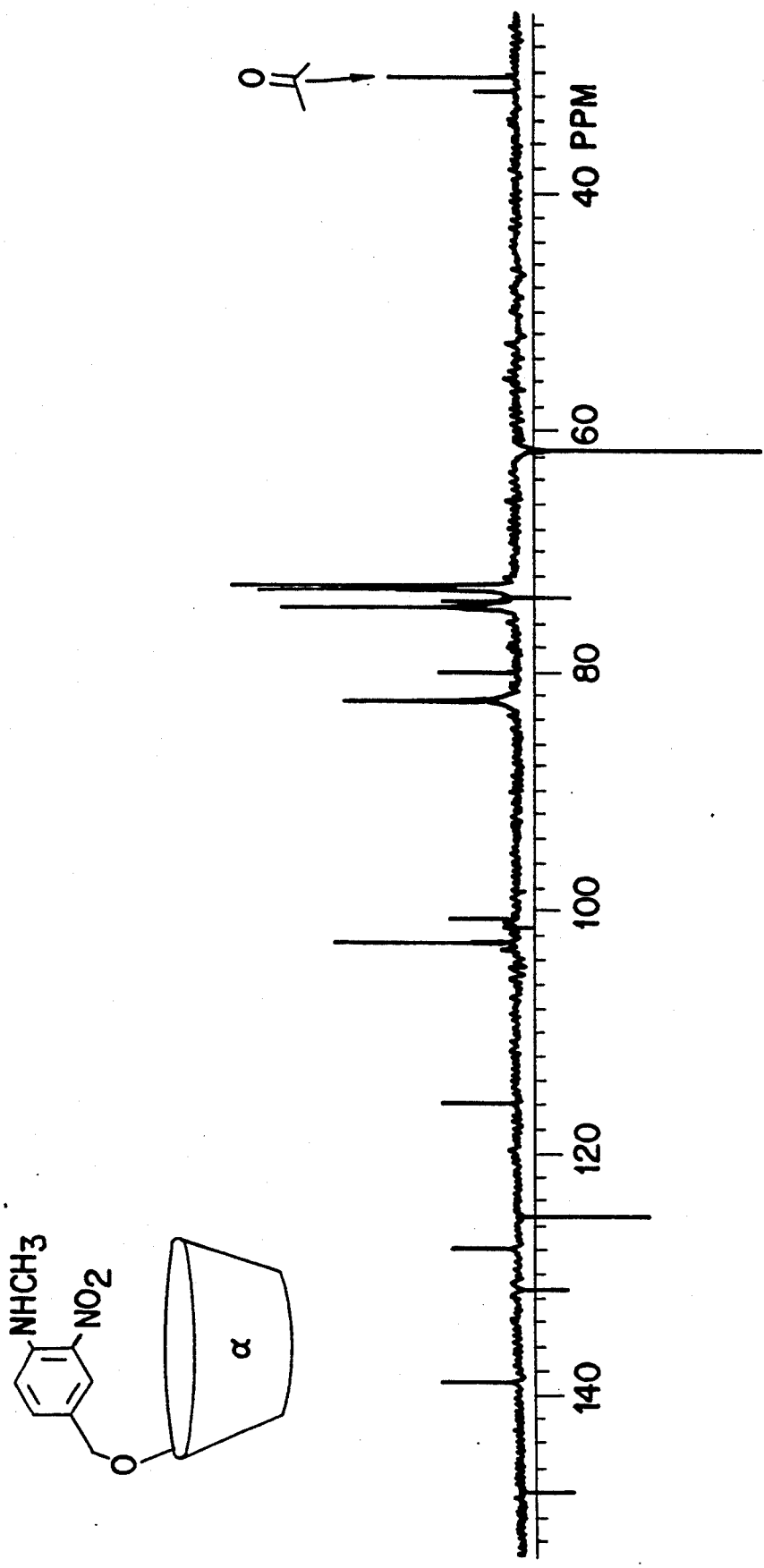
FIG. 19 shows a $^{13}$C(APT) NMR spectrum of the α-cyclodextrin analogue of structure 12 of Example 2.

FIG. 19 is the $^{13}$C(APT) NMR spectrum of the α-CD analogue of 12 of Example 2.

Figure 20:
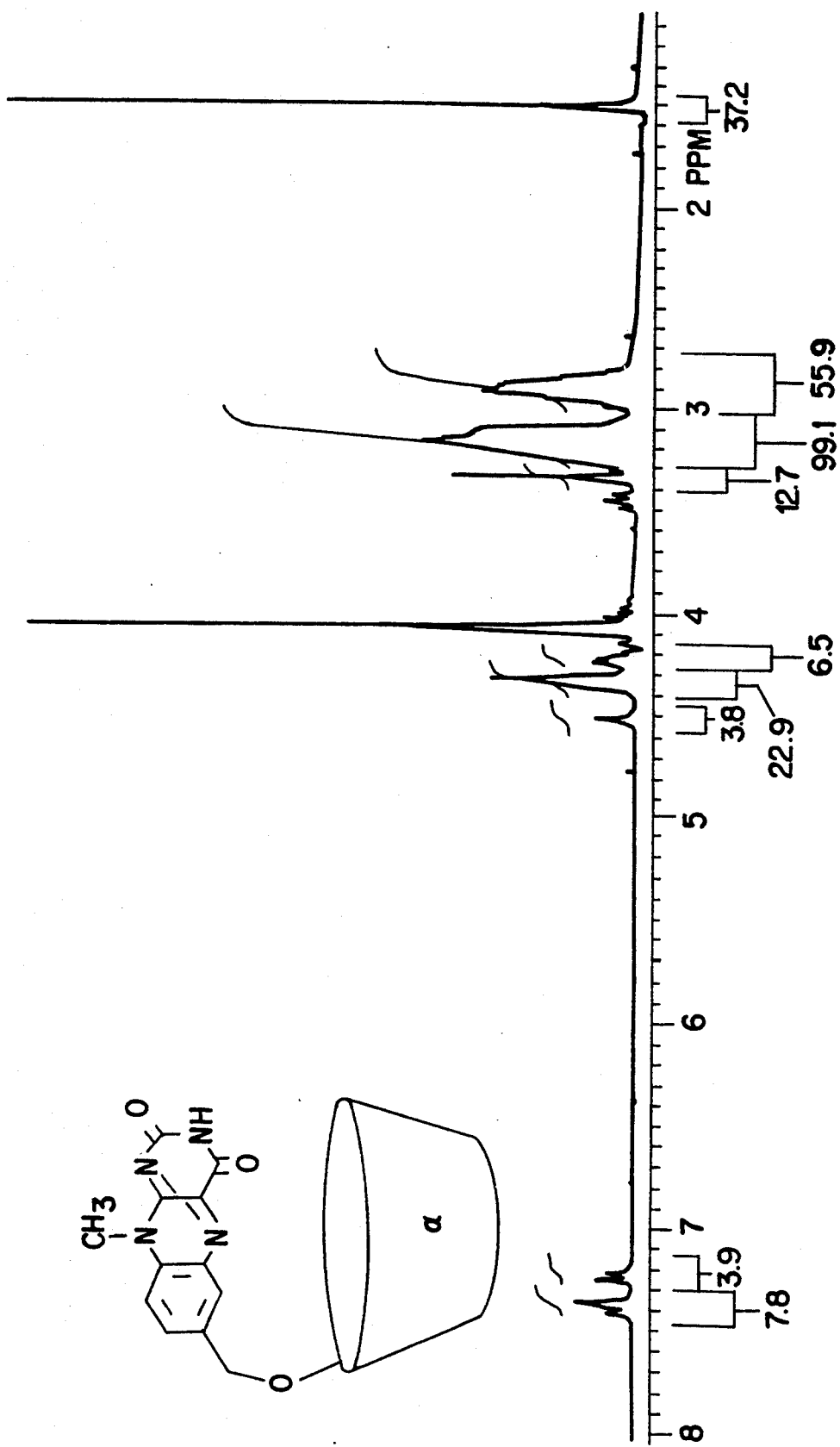
FIG. 20 shows a $^1$H NMR spectrum of the α-cyclodextrin analogue of structure 13 of Example 2.
Figure 21:
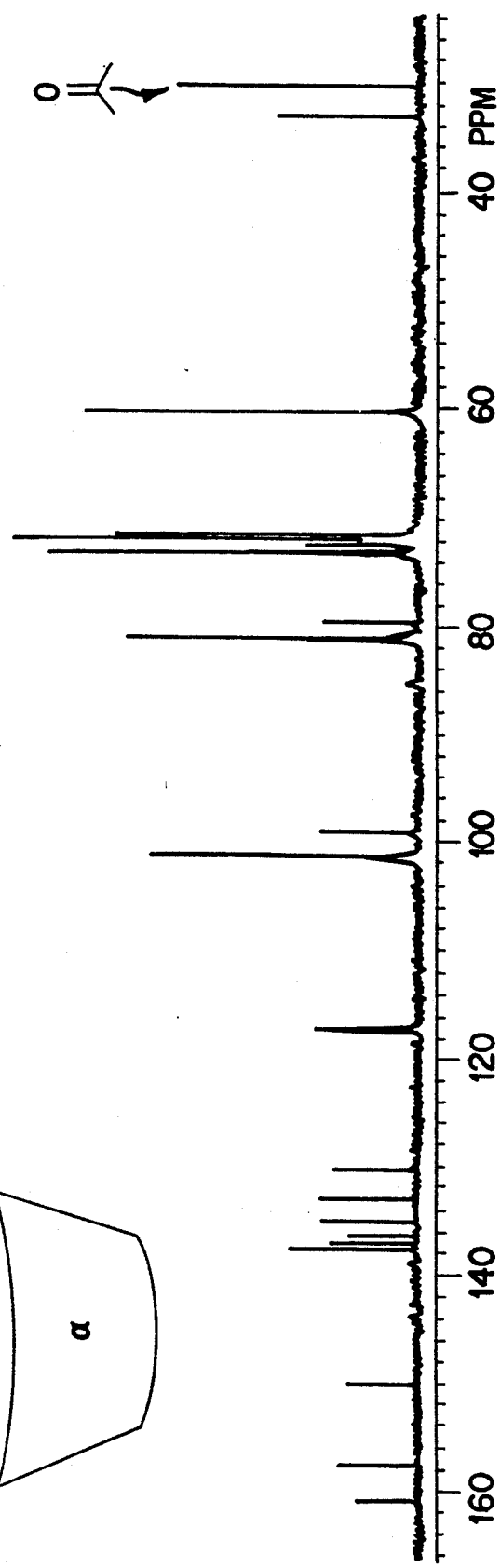
FIG. 21 shows a $^{13}$C NMR spectrum of the α-cyclodextrin analogue of structure 13 of Example 2.
Figure 22:
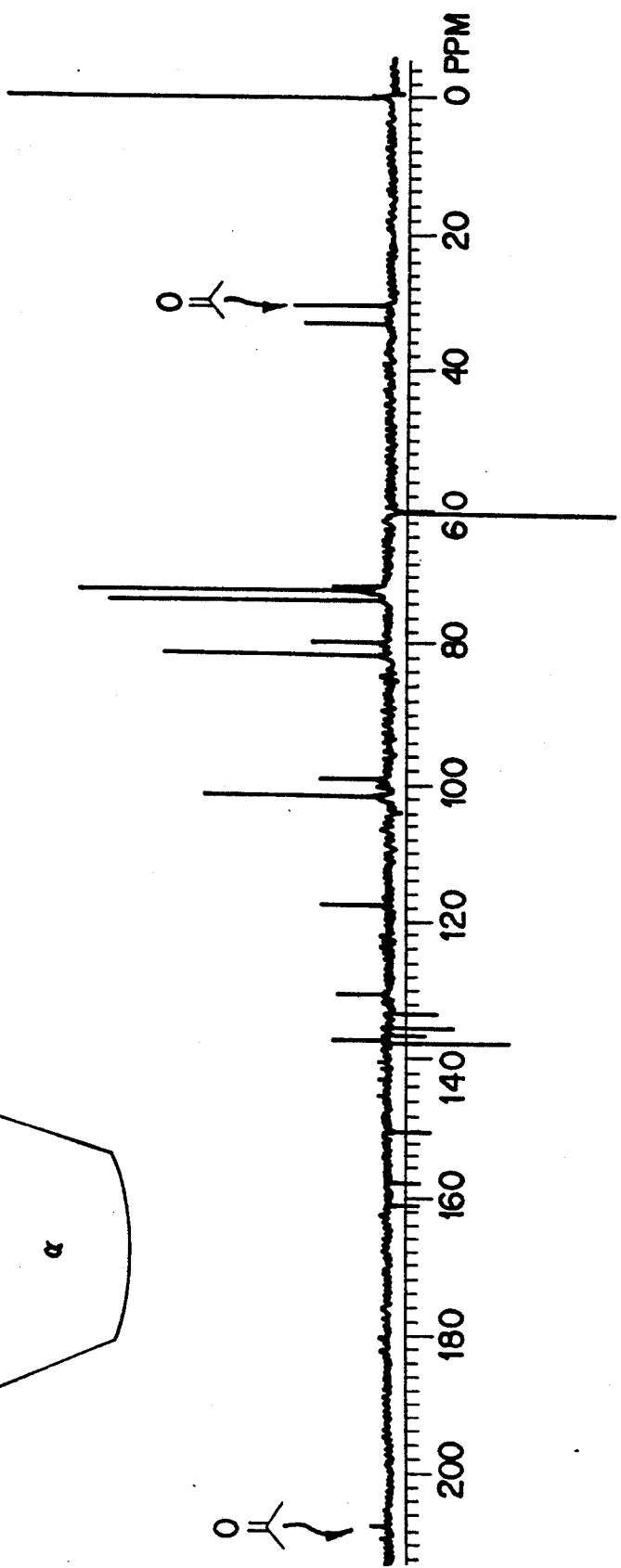
FIG. 22 shows a $^{13}$C(APT) NMR spectrum of the α-cyclodextrin analogue of structure 13 of Example 2.

FIGS. 20, 21 and 22 are $^1$H, $^{13}$C and $^{13}$C(APT) NMR spectra of the α-CD analogue of 13 of Example 2.

EXAMPLE 4

Comparison of Riboflavin and Flavocyclodextrin as Oxidation Catalysts

The oxidation of substrate benzylmercaptan ($4 \times 10^{-3}$M), by riboflavin ($5 \times 10^5$M) and by an artificial redox enzyme, 2-flavo-β-cyclodextrin ($5 \times 10^{-5}$M flavin), were compared at pH 10, $\mu$=0.68M, 30% CH$_3$OH at 25° C. by following the decrease of absorbancy of the thiol group at 440 nm with time.

Kinetic Measurements. Buffers were made up with distilled water employing reagent grade reagents. All kinetic studies were carried out at 25±0.1° C. in a mixed solvent of MeOH-H$_2$O. Reactions were followed under anaerobic conditions in stoppered (with SUBA SEAL SEPTA) cuvettes at 440 nm using Varian 2215 spectrophotometer with a thermostatted cell holder. A typical reaction mixture contained the desired concentration of flavin dissolved in 3 ml of buffer in the stoppered cuvette. This solution and substrate solution in CH$_3$OH were then deoxygenated separately with a stream of argon scrubbed of traces of O$_2$ by means of a vanadous ion trap for 45 minutes. The reaction was initiated by injecting substrate solution into cuvette. The data was collected and first order reaction rates were calculated with the Kinetic Calc program.

Figure 23:
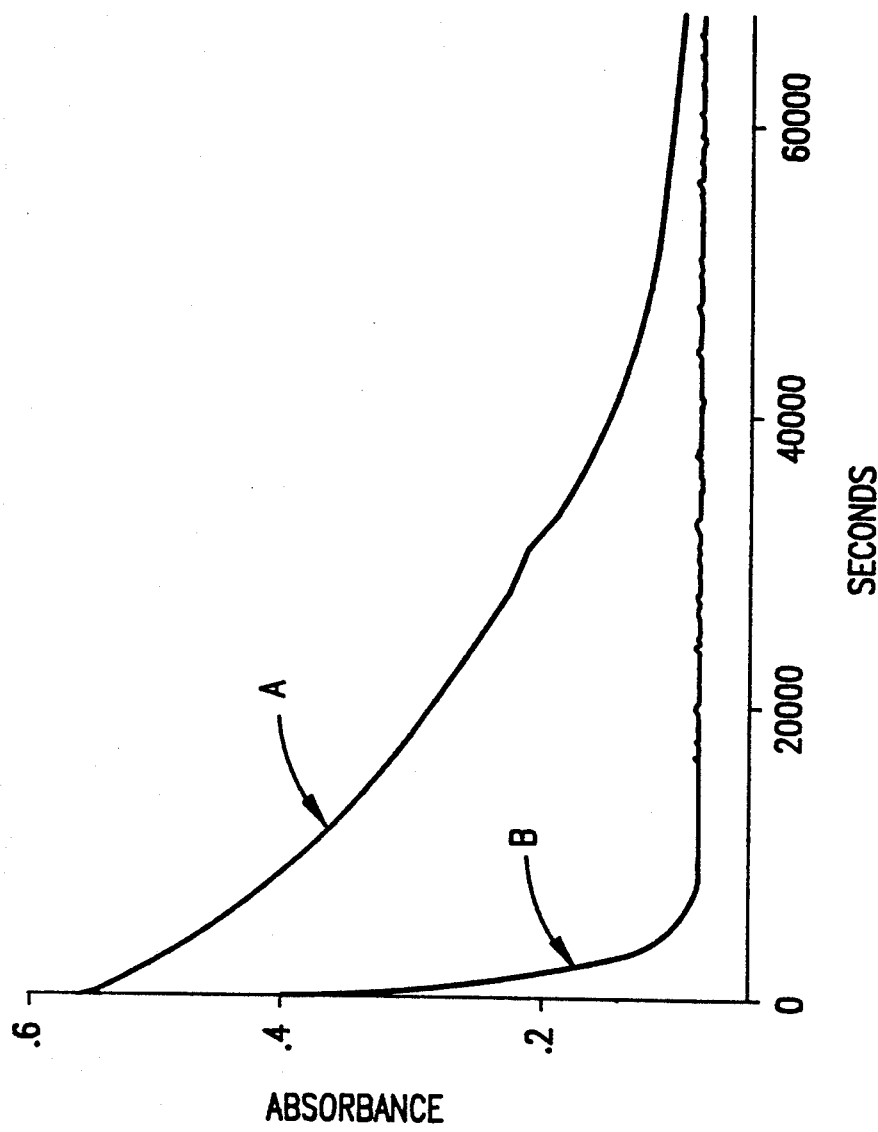
FIG. 23 shows the kinetics of the oxidation of benzyl mercaptan by riboflavin (A) and by 2-flavo-β-cyclodextrin (B).

As shown in FIG. 23, the flavocyclodextrin catalyzed a much more rapid and efficient (17-fold) oxidation of benzylmercaptan to bis-dibenzylsulfide than did the natural riboflavin.

EXAMPLE 5

Lineweaver-Burk Plots for the Oxidation of Benzyl Mercaptan by Flavocyclodextrin The concentration of artificial enzyme were kept constant and the concentration of substrate was varied. Pseudo-first-order rate constants were obtained from the decrease in the absorbance at 440 nm which represents the reduction of the flavin. Lineweaver-Burk plots were obtained by plotting 1/k$_1$ vs. the reciprocal of the substrate concentration. The straight line thus obtained has a slope of K$_{diss}$/K$_{cat}$ and a Y intercept equal to 1/k$_{cat}$ where K$_{diss}$ is the dissociation constant of the artificial enzyme-substrate complex and k$_{cat}$ is the turnover rate for the reaction of complexed substrate.

Figure 24:
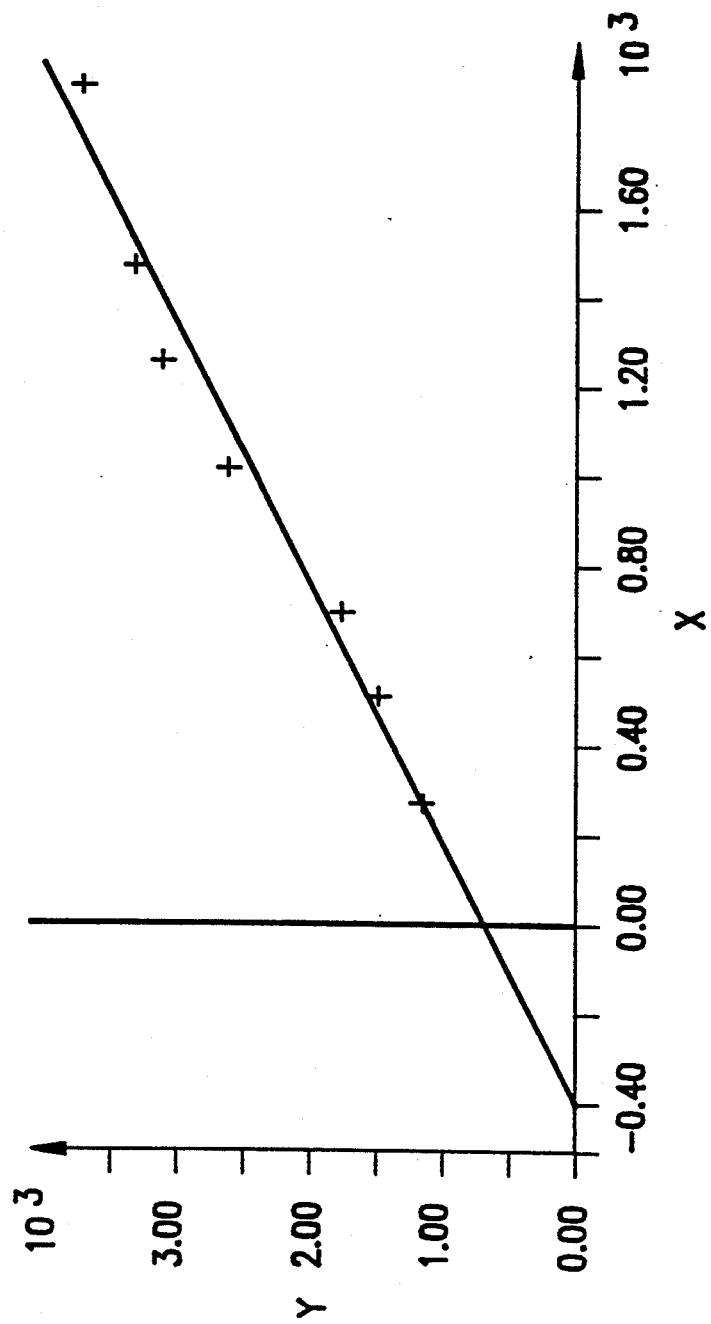
FIG. 24 shows the Lineweaver-Burk plot of the oxidation of benzyl mercaptan by 2-flavor-β-cyclodextrin.

The Lineweaver-Burk plot for the oxidation of benzylmercaptan ($4 \times 10^{-3}$M) by 2-flavo-β-cyclodextrin (flavin=$5 \times 10^{-5}$M) at pH 10.0, $\mu$=0.68M, 30% CH$_3$OH in water as solvent, is shown in FIG. 24. The X and Y values and the gradient and intercept data are reproduced below.

| bmb.enz Linear Regression Simple Weighting | | |
|---|---|---|
| Variable | Value | Std. Err. |
| Gradient | 1.71397E + 00 | 1.10622E − 01 |
| Intercept | 6.77296E + 02 | 1.25296E + 02 |
| X | Y | Calculated |
| 1  1.88700E + 03 | 3.73100E + 03 | 3.91156E + 03 |
| 2  1.44900E + 03 | 3.21500E + 03 | 3.16084E + 03 |
| 3  1.25000E + 03 | 3.03000E + 03 | 2.81976E + 03 |
| 4  1.00000E + 03 | 2.52000E + 03 | 2.39127E + 03 |
| 5  6.67000E + 02 | 1.68900E + 03 | 1.82051E + 03 |
| 6  5.00000E + 02 | 1.44900E + 03 | 1.53428E + 03 |
| 7  2.50000E + 02 | 1.11000E + 03 | 1.10579E + 03 |

The $k_{cat}$ of $1.47\times10^{-3}$ s$^{-1}$ and the Ka of 395.7M$^{-1}$ show that the acceleration in oxidation produced by the artificial enzyme is brought about by binding and catalysis similar to that carried out by natural protein enzymes.

EXAMPLE 6

Oxidation of Dihydronaphthylnicotinamide by 2-Flavo-β-Cyclodextrin

Figure 25:
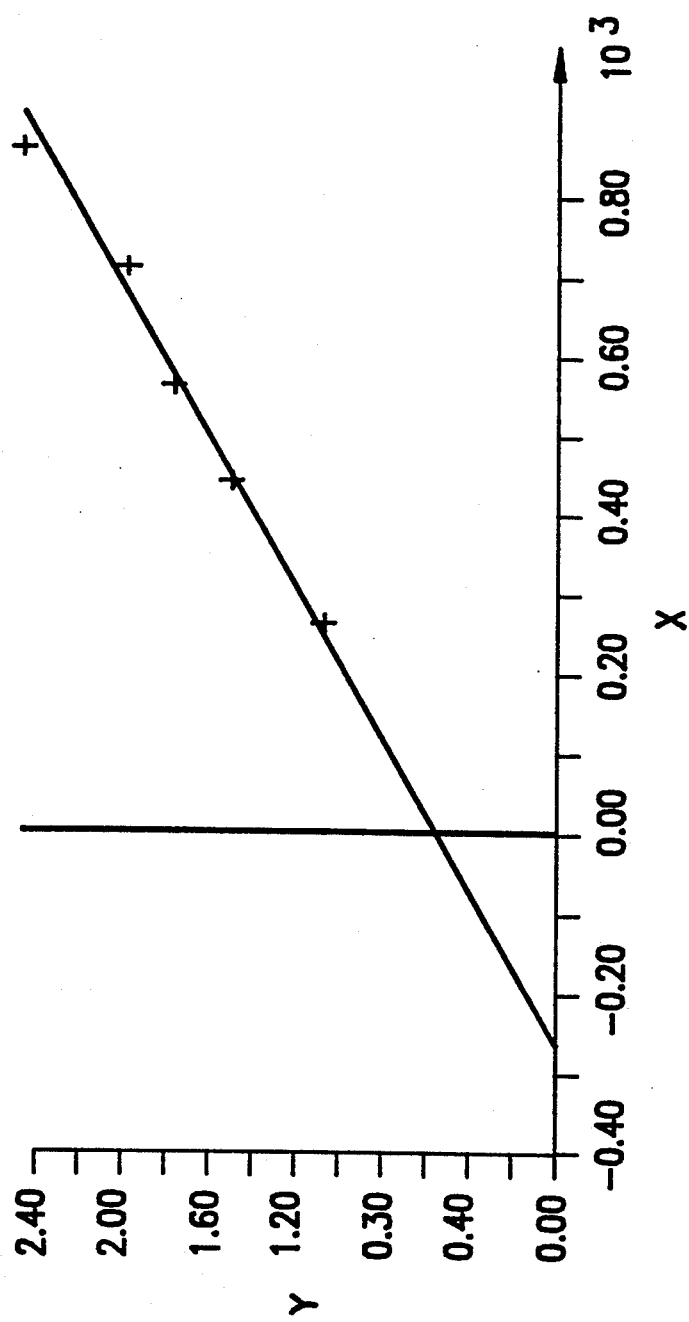
FIG. 25 shows the Lineweaver-Burk plot of the oxidation of the dihydronaphthylnicotinamide by 2-flavor-β-cyclodextrin.

FIG. 25 shows the Lineweaver-Burk plot for the oxidation of dihydronaphthylnicotinamide (a niacin analogue) at $4\times10^{-3}$M by 2-flavo-β-cyclodextrin (flavin=$5\times10^{-5}$M) at pH 7.0, $\mu$=0.08M, in 50% CH$_3$OH in water. The kinetic data are reproduced below.

The $k_{cat}$ of $2.82\times10^{-2}$ s$^{-1}$ and the Ka of 277M$^{-1}$ again demonstrate that the artificial enzyme behaves catalytically as does a natural protein enzyme.

| nabfir.enz Linear Regression Simple Weighting | | |
|---|---|---|
| Variable | Value | Std. Err. |
| Gradient | 2.12613E − 03 | 1.08678E − 04 |
| Intercept | 5.90273E − 01 | 6.45856E − 02 |
| X | Y | Calculated |
| 1  8.55000E + 02 | 2.44200E + 00 | 2.40811E + 00 |
| 2  6.99000E + 02 | 2.00400E + 00 | 2.07644E + 00 |
| 3  5.49000E + 02 | 1.78300E + 00 | 1.75752E + 00 |
| 4  4.27000E + 02 | 1.52300E + 00 | 1.49813E + 00 |
| 5  2.50000E + 02 | 1.11000E + 00 | 1.12180E + 00 |

We claim:

1. An artificial redox enzyme comprising a β-cyclodextrin covalently or electrostatically linked via an oxygen atom linked to ring position C-6 of an α-1,4-linked D-glucopyranose moiety of said cyclodextrin to at least one redox coenzyme or cofactor.

2. An artificial redox enzyme of claim 1, wherein said at least one redox coenzyme is covalently linked to said oxygen atom, and wherein said at least one redox coenzyme is selected from the group consisting of unsubstituted flavins, pyridines, pteridines, hemes, coenzyme Q, and derivatives thereof.

3. An artificial redox enzyme comprising an α-cyclodextrin covalently or electrostatically linked via an oxygen atom linked to ring position C-6 of an α-1,4-linked D-glucopyranose moiety of said cyclodextrin to at least one redox coenzyme or cofactor, wherein said coenzyme is a pyridine or derivative thereof.

4. An artificial redox enzyme comprising an α-cyclodextrin covalently or electrostatically linked via an oxygen atom linked to ring position C-6 of an α-1,4-linked D-glucopyranose moiety of said cyclodextrin to at least one redox coenzyme or cofactor, wherein said coenzyme is a pteridine or derivative thereof.

5. An artificial redox enzyme comprising an α-cyclodextrin covalently or electrostatically linked via an oxygen atom linked to ring position C-6 of an α-1,4-linked D-glucopyranose moiety of said cyclodextrin to at least one redox coenzyme or cofactor, wherein said coenzyme is a heme or derivative thereof.

6. An artificial redox enzyme comprising an α-cyclodextrin covalently or electrostatically linked via an oxygen atom linked to ring position C-6 of an α-1,4-linked D-glucopyranose moiety of said cyclodextrin to at least one redox coenzyme or cofactor, wherein said coenzyme is coenzyme Q or a derivative thereof.

7. An artificial redox enzyme of claim 1, 3, 4, 5 or 6, wherein said cofactor is electrostatically linked, and wherein said cofactor is selected from the group consisting of chromium, manganese, iron, cobalt, nickel, copper, zinc, rhodium, osmium, palladium and platinum metal ions.

8. An artificial redox enzyme of claim 1, 3, 4, 5 or 6 wherein said cyclodextrin has hydroxyl groups not linked to said coenzyme or cofactor that are derivatized.

9. An artificial redox enzyme of claim 8, wherein said derivatized hydroxyl groups are selected from the group consisting of O-alkyl, O-acyl, O-aryl, O-alkylsulfonyl, O-arylsulfonyl and O-(trialkylsilyl).

10. An artificial redox enzyme comprising a cyclodextrin covalently or electrostatically linked via an oxygen atom linked to ring position C-2 of an α-1,4-linked D-glycopyranose moiety of said cyclodextrin to a redox coenzyme or cofactor.

11. An artificial redox enzyme of claim 10, wherein said cyclodextrin is selected from the group consisting of α, β and γ-cyclodextrins.

12. An artificial redox enzyme of claim 10, wherein said redox coenzyme is covalently linked to said oxygen atom, and wherein said redox coenzyme is selected from the group consisting of unsubstituted flavins, pyridines, pteridines, hemes, coenzyme Q, and derivatives thereof.

13. An artificial redox enzyme of claim 10, wherein said cofactor is electrostatically linked to said oxygen atom, and wherein said cofactor is selected from the group consisting of chromium, manganese, iron, cobalt, nickel, copper, rhodium, osmium, palladium and platinum metal ions.

14. An artificial redox enzyme of claim 10, wherein said cyclodextrin has hydroxyl groups not linked to said coenzyme or cofactor that are derivatized.

15. An artificial redox enzyme of claim 14, wherein said derivatized hydroxyl groups are selected from the group consisting of O-alkyl, O-acyl, O-aryl, O-alkylsulfonyl, O-arylsulfonyl and O-(trialkylsilyl).

16. An artificial redox enzyme comprising a cyclodextrin covalently or electrostatically linked via an oxygen atom linked to ring position C-3 of an α-1,4-linked D-glucopyranose moiety of said cyclodextrin to a redox coenzyme or cofactor.

17. An artificial redox enzyme of claim 16, wherein said cyclodextrin is selected from the group consisting of α, β and γ-cyclodextrins.

18. An artificial redox enzyme of claim 16, wherein said redox coenzyme is covalently linked to said oxygen atom, and wherein said redox coenzyme is selected from the group consisting of unsubstituted flavins, pyridines, pteridines, hemes, coenzyme Q, and derivatives thereof.

19. An artificial redox enzyme of claim 16, wherein said cofactor is electrostatically linked to said oxygen atom, and wherein said cofactor is selected from the group consisting of chromium, manganese, iron, cobalt, nickel, copper, zinc, rhodium, osmium, palladium and platinum metal ions.

20. An artificial redox enzyme of claim 16, wherein said cyclodextrin has hydroxyl groups not linked to said coenzyme or cofactor that are derivatized.

21. An artificial redox enzyme of claim 20, wherein said derivatized hydroxyl groups are selected from the group consisting of O-alkyl, O-acyl, O-aryl, O-alkylsulfonyl, O-arylsulfonyl and O-(trialkylsilyl).

22. An artificial redox enzyme comprising a 2-cyclodextrin covalently or electrostatically linked via an oxygen atom linked to ring position C-6 of an α-1,4-linked D-glucopyranose moiety of said cyclodextrin to a redox coenzyme or cofactor.

23. An artificial redox enzyme of claim 22, wherein said redox coenzyme is covalently linked to said oxygen atom, and wherein said redox coenzyme is selected from the group consisting of unsubstituted flavins, pyridines, pteridines, hemes, coenzyme Q, and derivatives thereof.

24. An artificial redox of claim 22, wherein said cofactor is electrostatically linked to said oxygen atom, and wherein said cofactor is selected from the group consisting of chromium, manganese, iron, cobalt, nickel, copper, zinc, rhodium, osmium, palladium and platinum metal ions.

25. An artificial redox enzyme of claim 22, wherein said cyclodextrin has hydroxyl groups not linked to said coenzyme or cofactor that are derivatized.

26. An artificial redox enzyme of claim 25, wherein said derivatized hydroxyl groups are selected from the group consisting of O-alkyl, O-acyl, O-aryl, O-alkylsulfonyl, O-arylsulfonyl and O-(trialkylsilyl).

* * * * *

UNITED STATES PATENT AND TRADEMARK OFFICE
CERTIFICATE OF CORRECTION

PATENT NO. : 5,258,370

DATED : Nov. 2, 1993

INVENTOR(S) : D'Souza et al.

It is certified that error appears in the above-indentified patent and that said Letters Patent is hereby corrected as shown below:

On title page, item [56] "OTHER PUBLICATIONS"

Second col., line 12, "162" should be --152--.

Col. 2, line 1, "Soring" should be --Spring--.

Col. 3, beginning on line 3, "phenylpyrunic" should be --phenylpyruvic--.

Col. 3, line 41, "AND" should be --NAD--.

Col. 4, line 63, "$\beta$" should be --$\alpha$--.

Col. 5, line 39, "AND" should be --NAD--.

Col. 15, line 36, "was in" should be --was hydrogenated in--.

Col. 15, line 56, "6 60.3," should be --60.3,--.

UNITED STATES PATENT AND TRADEMARK OFFICE
CERTIFICATE OF CORRECTION

PATENT NO. : 5,258,370
DATED : Nov. 2, 1993
INVENTOR(S) : D'Souza et al

It is certified that error appears in the above-indentified patent and that said Letters Patent is hereby corrected as shown below:

<u>In the Claims</u>:
Column 19,
Claim 22, "2-" should be -- $\gamma$- --.

Signed and Sealed this

Third Day of May, 1994

Attest:

BRUCE LEHMAN

Attesting Officer

Commissioner of Patents and Trademarks